United States Patent
Gage et al.

(10) Patent No.: US 6,300,488 B1
(45) Date of Patent: Oct. 9, 2001

(54) MODIFIED LEPIDOPTERAN RECEPTORS AND HYBRID MULTIFUNCTIONAL PROTEINS FOR USE IN TRANSCRIPTION AND REGULATION OF TRANSGENE EXPRESSION

(75) Inventors: Fred H. Gage; Steven T. Suhr, both of La Jolla, CA (US)

(73) Assignee: The Salk Institute for Biological Studies, La Jolla, CA (US)

(*) Notice: Subject to any disclaimer, the term of this patent is extended or adjusted under 35 U.S.C. 154(b) by 0 days.

(21) Appl. No.: 08/891,298

(22) Filed: Jul. 10, 1997

(51) Int. Cl.$^7$ .......................... C07N 21/04; C07N 15/00; C07N 15/63

(52) U.S. Cl. .................. 536/23.4; 435/69.1; 435/320.1; 435/325; 435/252.3; 435/172.3; 536/23.1; 536/23.4

(58) Field of Search ................. 435/69.1, 320.1, 435/325, 252.3, 172.3; 536/23.1, 23.4

(56) References Cited

U.S. PATENT DOCUMENTS

| | | |
|---|---|---|
| 4,394,448 | 7/1983 | Szoka, Jr. et al. .................. 435/172 |
| 4,399,216 | 8/1983 | Axel et al. ............................ 435/6 |
| 4,405,712 | 9/1983 | Vande Woode et al. .............. 435/5 |
| 4,619,794 | 10/1986 | Hauser .............................. 264/4.1 |
| 4,634,665 | 1/1987 | Axel et al. ........................... 435/68 |
| 4,650,764 | 3/1987 | Temin et al. ...................... 435/240 |
| 4,870,009 | 9/1989 | Evans et al. ........................ 435/70 |
| 4,952,496 | 8/1990 | Studier et al. ..................... 435/91 |
| 4,981,784 | 1/1991 | Evans et al. .......................... 435/6 |
| 5,071,773 | 12/1991 | Evans et al. ...................... 436/501 |
| 5,171,671 | 12/1992 | Evans et al. ..................... 435/69.1 |
| 5,252,479 | 10/1993 | Srivastava ...................... 435/235.1 |
| 5,399,346 | 3/1995 | Anderson et al. .............. 424/93.21 |
| 5,739,018 * | 4/1998 | Miyanohara et al. ............ 435/172.3 |
| 5,747,323 * | 5/1998 | Darlix et al. .................... 435/235.1 |
| 5,747,338 * | 5/1998 | Giese et al. ....................... 435/348 |
| 5,891,431 * | 4/1999 | Palli et al. ........................ 424/93.2 |

FOREIGN PATENT DOCUMENTS

| | | | |
|---|---|---|---|
| WO 89/05345 | 6/1989 | (WO) | ........................... C12N/5/00 |
| WO 90/06997 | 6/1990 | (WO) | ......................... C12N/15/00 |
| WO 92/05266 | 4/1992 | (WO) | ......................... C12N/15/86 |
| WO 92/07573 | 5/1992 | (WO) | ......................... A61K/35/12 |
| WO 92/14829 | 9/1992 | (WO) | ......................... C12N/15/87 |
| WO 96/37609 | 11/1996 | (WO) | ......................... C12N/15/12 |

OTHER PUBLICATIONS

George et al., Current Methods in Sequence Comparison and Analysis, Macromolecular Sequencing and Synthesis, Selected Methods asd Applications. Edited by David H. Schlesinger, Alan R. Liss, In., New York. pp. 124–149, 1988.*

Adam and Miller, "Identification of a Signal in a Murine Retrovirus That Is Sufficient for Packaging of Nonretroviral RNA into Virions" *J. Virol.*, 62(10):3802–3806 (1988).

Baim et al. "A chimeric mammalian transactivator based on the lac repressor that is regulated by temperature and isoproply β–D–thiogalactopyranoside" *PNAS*, 88:5072–5076 (1991).

Barklis et al., "Chromosomal Position or Virus Mutation Permits Retrovirus Expression in Embryonal Cells" *Cell*, 47:391–399.

Bosselman, et al., "Replication–Defective Chimeric Helper Proviruses and Factors Affecting Generation of Competent Virus: Expression of Moloney Murine Leukemia Virus Structural Genes via the Metallothionein Promoter" *Molecular and Cellular Biology*, 7(5):1797–1806 (1987).

Brent and Ptashne, "A Eukaryotic transcriptional Activator Bearing the DNA Specificity of a Prokaryotic Repressor" *Cell*, 43:729–736 (1985).

Bugge et al. (1992) "RXRα, a promiscuous partner of retinoic acid and thyroid receptors" *EMBO J.*, 11(4):1409–1418 (1992).

Cho et al. "Mosquito Ecdysteroid Receptor: Analysis of the cDNA and Expression During Vitellogenesis" *Insect Biochem Molec. Biol.*, 25(1):19–27 (1995).

Danos and Mulligan, "Safe and efficient generation of recombinant retroviruses with amphotropic and ecotropic host ranges" *PNAS*, 85:6460–6464 (1988).

Evans, R., "The Steroid and Thyroid Hormone Receptor Superfamily" *Science*, 240:889–895 (1988).

Friedmann, "Progress Toward Gene Therapy" *Science*, 244: 1275–1281 (1989).

Fujiwara et al. "Cloning of an Ecdysone Receptor Homolog from *Manduca sexta* and the Developmental Profile of Its mRNA in Wings" *Insect Biochem. Molec. Biol.*, 25(7):845–856 (1995).

Furth et al. "Temporal control of gene expression in transgenic mice by a tetracycline–responsive promoter" *PNAS*, 91:9302–9306 (1994).

Gossen et al. "Tight control of gene expression in mammalian cells by tetracycline–responsive promotors" *PNAS*, 89:5547–5551 (1992).

(List continued on next page.)

*Primary Examiner*—Yvonne Eyler
*Assistant Examiner*—Nirman S. Basi
(74) *Attorney, Agent, or Firm*—Stephen E. Reiter; Foley & Lardner

(57) ABSTRACT

In accordance with the present invention, it has been discovered that nuclear receptor proteins isolated from the silk moth *Bombyx mori* (bR) are useful for the regulation of transgene expression. bR is generally thought to be a strong transcriptional regulator within cells of the silk moth. In accordance with the present invention, it has been discovered that bR is also functional in mammalian cells. It has further been discovered that the addition of activation domains to the bR open-reading frame enhances the activity of the ligand modulated regulator to afford high-level transcriptional induction. Further modifications to the bR ligand binding domain result in receptors with unique tranactivational characteristics.

39 Claims, 7 Drawing Sheets

OTHER PUBLICATIONS

Gossen et al. "Control of gene activity in higher eukaryotic cells by prokaryotic regulatory elements" *TIBS,* 18:471–475 (1993).

Gossen et al. "Transcriptional Activation by Tetracyclines in Mammalian Cells" *Science,* 268:1766–1769 (1995).

Harrison, S., "A Structural Taxonomy of DNA–binding Domains," *Nature,* 353:715–719 (1991).

Hollenberg and Evans, "Multiple and Cooperative Trans–Activation Domains of the Human Glucocorticoid Receptor," in *Cell,* 55:899–906 (1988).

Hoshimaru et al., "Differentiation of the immortalized adult neuronal progenitor cell line HC2S2 into neurons by regulatable suppression of the v–myc oncogene" *PNAS* 93(4):1518–1523 (1996).

Imhof et al., "Cloning of a *Chironomus tentans* cDNA Encoding a Protein (cEcRH) Homologous to the *Drosophila melanogaster* Ecdysteroid Receptor (dEcR)," *Insect Biochem. Molec. Biol.* 25:115–124 (1993).

Issemann et al., "The retinoid X receptor enhances the function of the peroxisome proliferator activated receptor," *Biochimie.* 75:251–256 (1993).

Jacobs, "Determination of the base recognition positions of zinc fingers from sequence analysis," *EMBO J.,* 11(12): 4507–4517 (1992).

Jacobs and Michaels, "Zinc Finger Gene Database," *New Biol.,* 2(6):583 (1990).

Jaenisch, R., "Transgenic Animals," *Science,* 240:1468–1474 (1988).

Keegan et al., "Separation of DNA Binding from the Transcription–Activating Function of a Eukaryotic Regulatory Protein," *Science,* 231:699–704 (1986).

Kliewer et al., "Retinoid X receptor interacts with nuclear receptors in retinoic acid, thyroid hormone and vitamins $D_3$ signalling," *Nature,* 355:446–449 (1992).

Klug and Rhodes, "'Zinc fingers': a novel protein motif for nucleic acid recognition," *Trends Biochem. Sci.,* 12:464–469 (1987).

Ladias and Karathanasis, "Regulation of the Apolipoprotein AI Gene by ARP–1, a Novel Member of the Steroid Receptor Superfamily," *Science,* 251:561–565 (1991).

Leid et al, "Purification, Cloning, and RXR Identity of the HeLa Cell Factor with Which RAR or TR Heterodimerizes to Bind Target Sequences Efficiently," *Cell,* 68:377–395 (1992).

Leonard et al., "Characterization of Somatostatin Transactivating Factor–1, a Novel Homeobox Factor That Stimulates Somatostatin Expression in Pancreatic Islet Cells," *Mol. Endo.,* 7:1275–1283 (1993).

Markowitz, et al., "A Safe Packaging Line for Gene Transfer: Separating Viral Genes on Two Different Plasmids," *Journal of Virology,* 61(4):1120–1124 (1988).

Marks et al., "H2RIIBP (RXRβ) heterodimerization provides a mechanism for combinational diversity in the regulation of retinoic acid and thyroid hormone responsive genes," *EMBO J.* 11(4):1419–1435 (1992).

Miller, "Retrovirus Packaging Cells," *Human Gene Therapy,* 1:5–14 (1990).

Miyajima et al., "Identification of two novelmembers of erbA superfamily by molecular cloning: the gene products of the two are highly related to each other," *NAR,* 16(23):11057–11074 (1988).

Mlodzik et al., "The Drosophila seven–up Gene, a Member of the Steroid Receptor Gene Superfamily, Controls Photoreceptor Cells Fates," *Cell,* 60:211–224 (1990).

Mulligan, "The Basic Science of Gene Therapy," *Science,* 260:926–932 (1993).

Mulligan et al., "Synthesis of rabbit β–globin in cultured monkey kidney cells following infection with a SV40 β–globin recombinant genome," *Nature,* 277:108–114 (1979).

Nakamura et al., "DNA Sequence of the Gene for the Outer Membrance Lipoprotein of *E. coli:* an Extremely AT–Rich Promoter," *Cell,* 18:1109–1117 (1979).

Naldini et al., "In Vivo Gene Delivery and Stable Transduction of Nondividing Cells by a Lentriviral Vector," *Science,* 272:165–320 (1996).

O'Gorman et al., "Recombinase–Mediated Gene Activation and Site–Specific Integration in Mammalian Cells," *Science,* 251: 1351–1355 (1991).

Palli et al., "Cloning and Developmental Expression of Chroistoneura Hormone Receptor 3, and Ecdysone–Inducible Gene and a Member of the Steroid Hormone Receptor Superfamily," *Insect Biochem. Molec. Biol.,* 26(5):485–499 (1996).

Pear et al., "Production of high–titer helper–free retroviruses by transient transfection," *PNAS,* 90:8392–8396 (1993).

Rosenberg et al., "Grafting Genetically Modified Cells to the Damaged Brain: Restorative Effects of NGF Expression," *Science,* 242:1575–1578 (1988).

Ross et al., "Targeted expression of a toxin gene to adipose tissue: Transgenic mice resistant to obesity," *Genes and Development,* 7:1318–1324 (1993).

Scott et al., "The structure and function of the homeodomain," *Biochem. Biophys. Acta,* 989:25–48 (1989).

Shackleford et al., "Construction of a clonable, infectious, and tumorigenic mouse mammary tumor virus provirus and a derivative genetic vector," *PNAS,* 85:9655–9659 (1988).

Shimohama et al., "Grafting genetically modified cells into the rat brain: characteristics of *E. coli* β–galactosidase as a reporter gene," *Brain Res Mol Brain Res,* 5:271–278 (1989).

Shockett et al., "A modified tetracycline–regulated system provides autoregulatory, inducible gene expression in cultured cells and transgenic mice," *PNAS,* 92:6522–6526 (1995).

Sladek et al., "Liver–enriched transcription factor HNF–4 is a novel member of the steroid hormone receptor superfamily," in *Genes & Development,* 4:2353–2365 (1990).

Studier et al., "[6] Use of T7 RNA Polymerase to Direct Expression of Cloned Genes," *Meth. Enzymol.,* 185:60–89 (1990).

Suhr et al., "Gene Therapy for Neurologic Disease," *Arch. of Neurol.,* 50:1252–1268 (1993).

Swevers et al., "The Silkmoth Homolog* of the Drosophila Ecdysone Receptor (B1 Isoform): Cloning and Analysis of Expression during Follicular Cell Differentiation," *Insect Biochem. Molec. Biol.,* 25(7):857–866 (1995).

Wang et al., "Coup transcription factor is a member of the steriod receptor superfamily," *Nature,* 340:163–166 (1989).

Watanabe, et al., "Construction of a Helper Cell Line for Avian Reticuloendotheliosis Virus Cloning Vectors," *Molecular and Cellular Biology,* 3(12):2241–2249 (1983).

Webster et al., "The Yeast $UAS_G$ Is a Transcriptional Enhancer in Human HeLa Cells in the Presence of the GAL4 Trans–Acitvator," *Cell,* 52:169–178 (1988).

Webster et al., "The Hormone–Binding Domains of the Estrogen and Glucocorticoid Receptors Contain an Inducible Transcription Activation Function," *Cell,* 54:199–207 (1988).

Wong et al., "Human GM–CSF: Molecular Cloning of the Complmentray DNA and Purification of the Natural and Recombianat Proteins" *Science,* 228:810–815 (1985).

Yu et al., "RXRβ: A Coregulator That Enhances Binding of Retinoic Acid, Thyroid Hormone, and Vitamin D Receptors to Their Cognate Response Elements," *Cell,* 67:1251–1266 (1991).

Zhang et al., "Retinoid X receptor is an auxilary protein for thyroid hormone and retinoic acid receptors," *Nature,* 355:441–446 (1992).

* cited by examiner

MODIFIED LEPIDOPTERAN RECEPTORS AND HYBRID MULTIFUNCTIONAL PROTEINS FOR USE IN TRANSCRIPTION AND REGULATION OF TRANSGENE EXPRESSION

ACKNOWLEDGMENT

This invention was made with Government support under Grant No. AG 10435, awarded by the National Institutes of Health. The Government has certain rights in the invention.

FIELD OF THE INVENTION

The present invention relates to methods in the field of recombinant DNA technology, and products related thereto. In a particular aspect, the invention relates to methods for modulating the expression of exogenous genes in mammalian systems, and products useful therefor.

BACKGROUND OF THE INVENTION

In the field of genetic engineering, precise control of gene expression is an invaluable tool for studying, manipulating and controlling development and other physiological processes. For example applications for regulated gene expression in mammalian systems include inducible gene targeting, overexpression of toxic and teratogenic genes, anti-sense RNA expression, and gene therapy (see, for example, Jaenisch, R. (1988) *Science* 240, 1468–1474). For cultured cells, glucocorticoids and other steroids have been used to induce the expression of a desired gene.

As another means for controlling gene expression in mammalian systems, an inducible tetracycline regulated system has been devised and utilized in transgenic mice, whereby gene activity is induced in the absence of the antibiotic and repressed in its presence (see, e.g, Gossen et al. (1992) *PNAS* 89, 5547–5551; Gossen et al.(1993) *TIBS* 18, 471–475; Furth et al. (1994) *PNAS* 91 9302–9306; and Shockett et al. (1995) *PNAS* 92, 6522–6526). However, disadvantages of the inducible tetracycline system include the requirement for continuous administration of tetracycline to repress expression and the slow clearance of antibiotic from bone, which interferes with regulation of gene expression. While this system has been improved by the recent identification of a mutant tetracycline repressor which acts conversely as an inducible activator, the pharmacokinetics of tetracycline may hinder its use during development when a precise and efficient "on-off" switch is essential (see, e.g., Gossen et al. (1995) *Science* 268, 1766–1769).

Accordingly, there is a need in the art for improved systems to precisely modulate the expression of exogenous genes in mammalian subjects. For example, a non-mammalian-based transcription regulating system would be extremely desirable for general application to transgene regulation in in vitro, ex vivo, and in vivo applications, as well as transgenic animals. A system that is simple, compact and dependent on ligands which are relatively inexpensive, readily available and of low toxicity in animals would prove useful for stimulation of regulated systems.

BRIEF DESCRIPTION OF THE INVENTION

In accordance with the present invention, it has been discovered that nuclear receptor proteins isolated from the silk moth *Bombyx mori* (bR) are useful for the regulation of transgene expression. bR is generally thought to be a strong transcriptional regulator within cells of the silk moth. In accordance with the present invention, it has been discovered that bR is also functional in mammalian cells. It has further been discovered that the addition of activation domains to the bR open-reading frame (VbR) enhances the activity of the ligand modulated regulator to afford high-level transcriptional induction (see, e.g., FIG. 1A). Further modifications to the bR ligand binding domain result in receptors with unique transactivation characteristics (see, e.g., FIG. 1B).

In accordance with another aspect of the present invention, hybrid proteins produced by fusion of modified bRs with other ligand-regulated proteins have been found to be capable of high level, regulated transactivation of sequences controlled by both hormone response elements and tetracycline operators. VbR variants and hybrid proteins (see, e.g., FIG. 1C), in combination with the appropriate promoters and transgenes, can be introduced into target cells by common methods such as transfection of plasmids or by virus mediated gene transfer. The small size and simplicity of these proteins makes them particularly attractive for use in retroviral vectors.

Invention methods provide for regulated gene expression by exogenous non-mammalian inducers, and therefor can be advantageously employed in a variety of in vivo and in vitro mammalian expression systems. For example, inducible expression of cre recombinase in transgenic mammals, in accordance with invention methods, would enable those of skill in the art to accomplish temporally specific inducible gene targeting of the adult or the developing embryo (see, for example, O'Gorman et al. (1991) *Science* 251, 1351–1355).

LINX: which encodes the tet-transactivator (TTA),

VbR: which encodes VbR,

TTMT: which encodes the TTA-VbR fusion protein, and

TTMT-2V: similar to TTMT but with two VP16 t-domains.

Figure 2A:
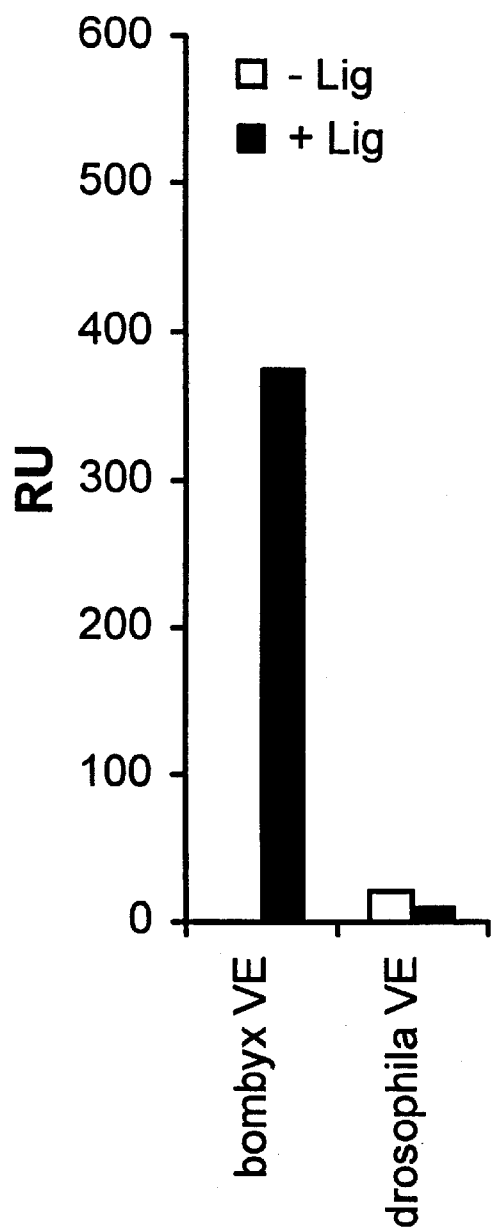
FIG. 2A shows the induction of fusion proteins (VP16 activation domain fused to either Drosophila ecdysone receptor (dVEcR) or *Bombyx mori* nuclear receptor derived (VbR)) with 5 µg/ml tebufenozide in the absence of exogenous dimer partners.
Figure 2B:
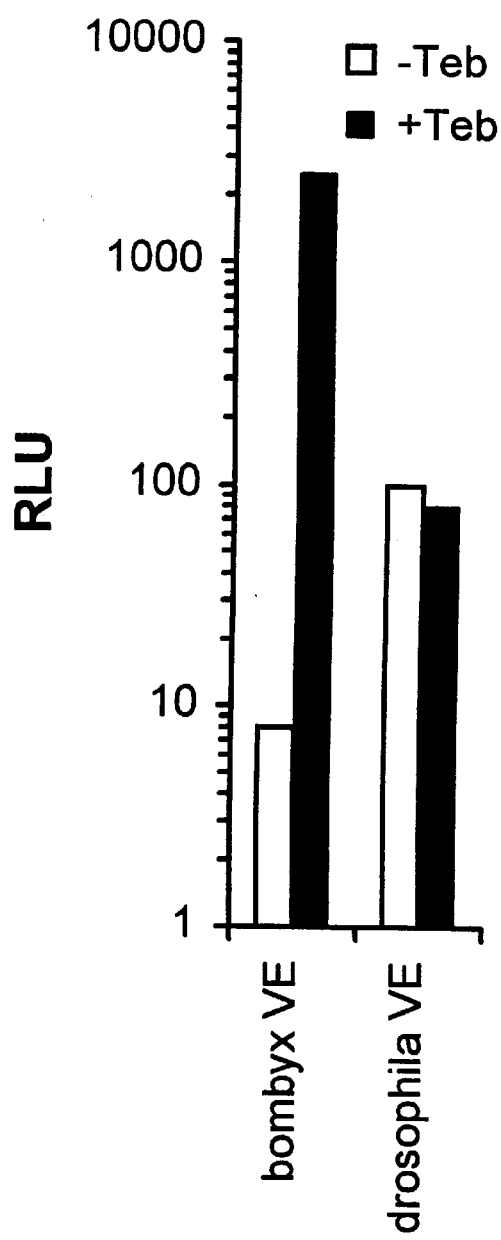
FIG. 2B shows that a peptide derived from *Bombyx mori* responds to tebufenozide (teb) with greater than 200-fold induction, while Drosophila EcR responds weakly, it at all.
Figure 2C:
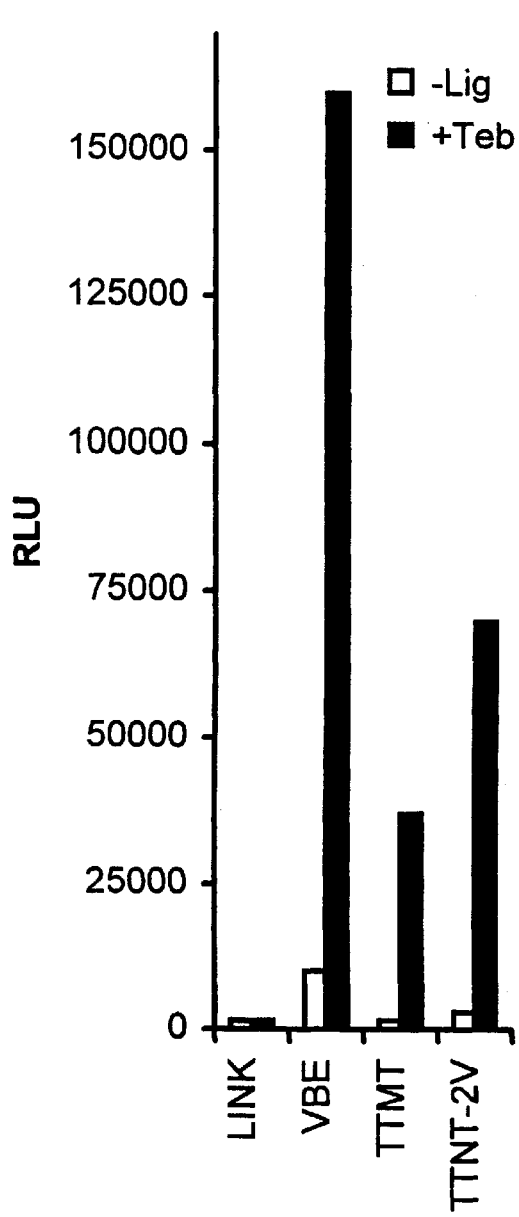
FIG. 2C illustrates the action of tebufenozide (teb) on the expression of EcRE-Luc reporter when co-transfected with the following receptors.
Figure 2D:
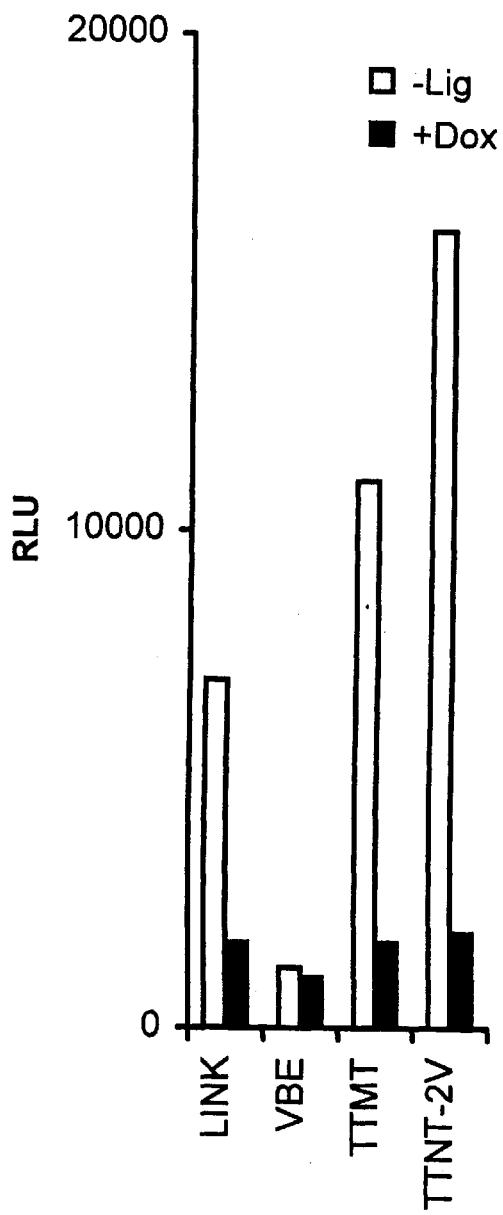

FIG. 2D depicts the same experiment illustrated in FIG. 2C, utilizing a TetO-Luc reporter, which responds only to TTA or fusion proteins in the absence of doxycycline.

Figure 2E:
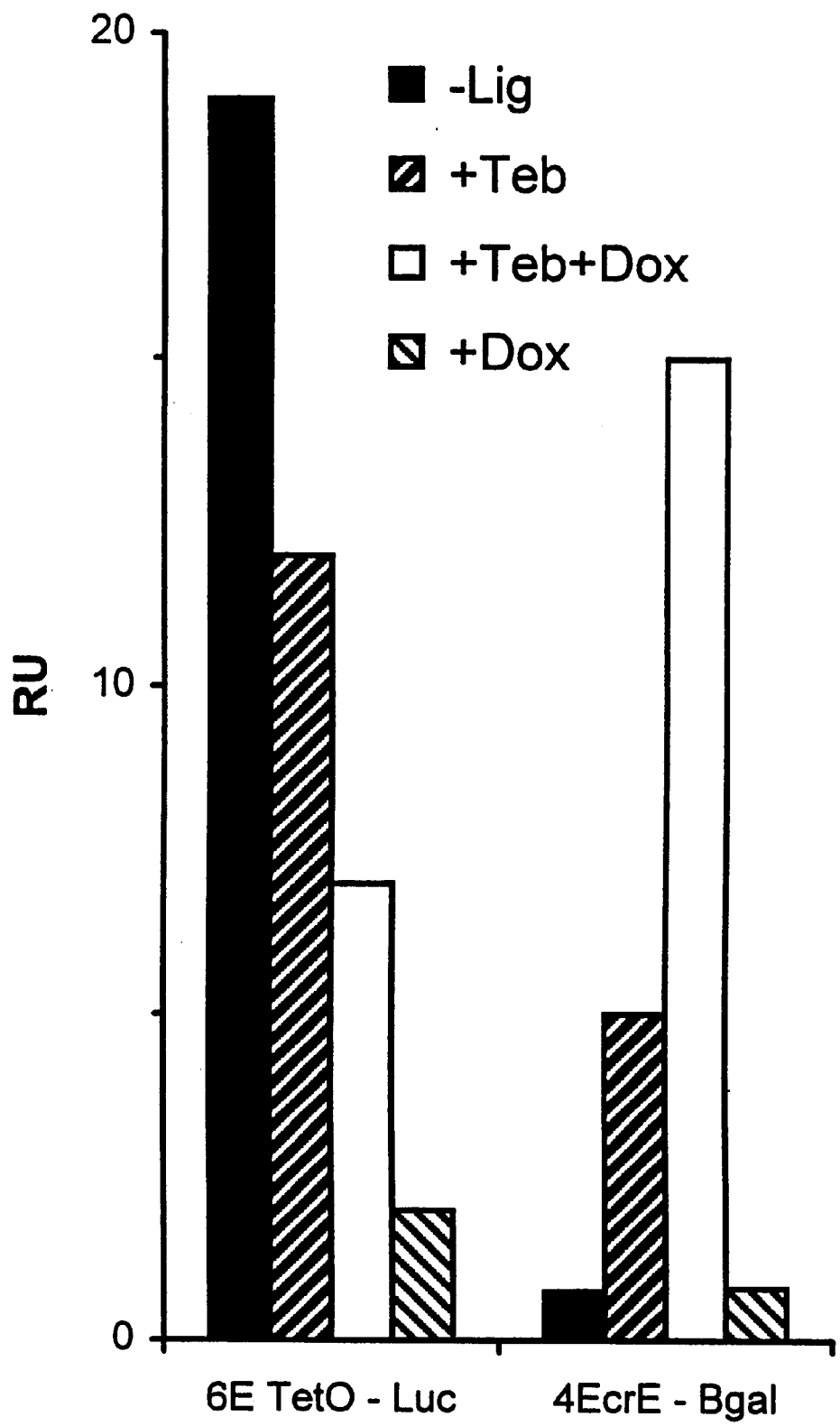

FIG. 2E shows the results of an experiment employing CV-1 cells transfected with TTMT and two reporters: 6TetO-luc and 4-EcRE-bgalactosidase.

Figure 3:
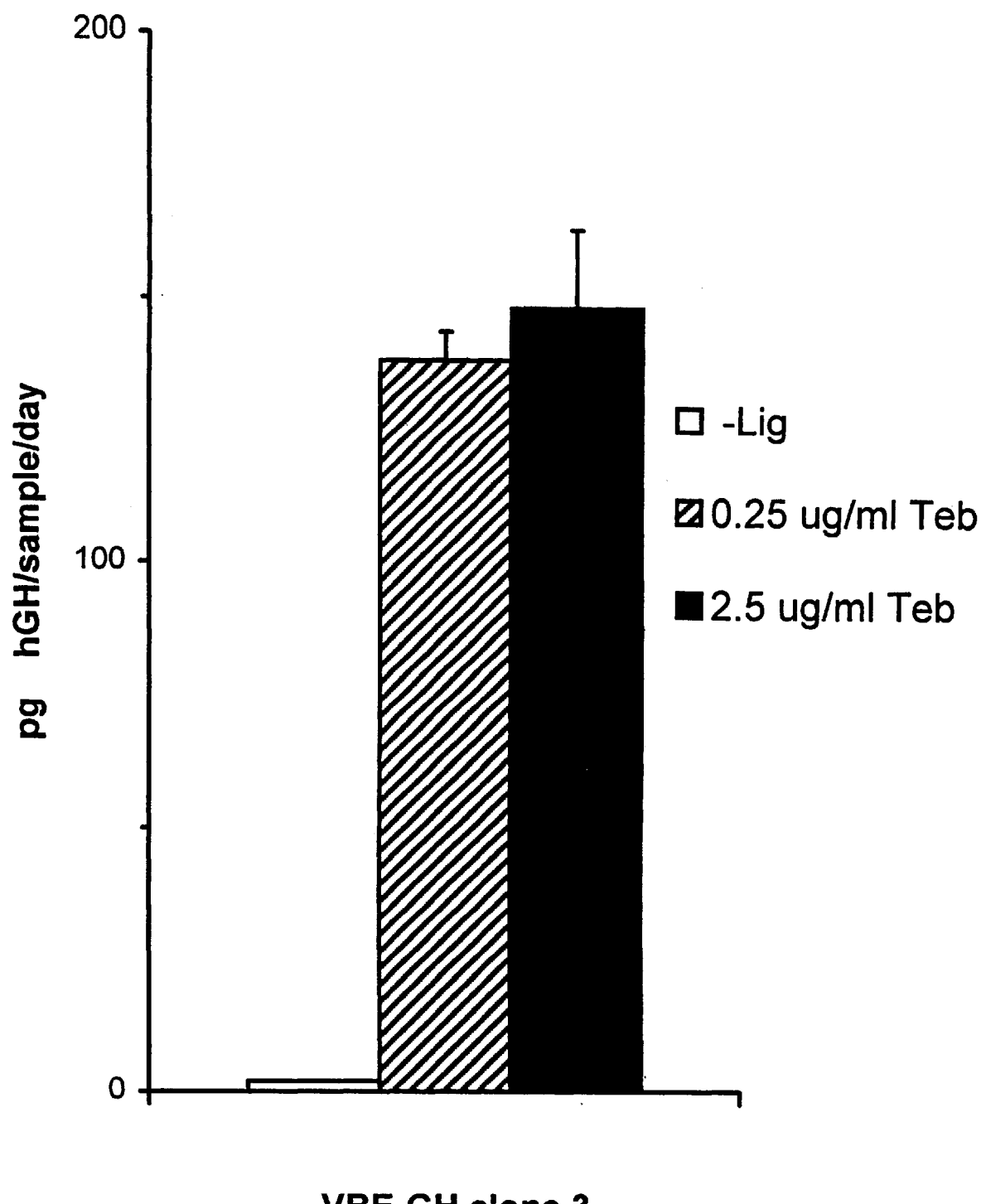

FIG. 3 shows that lower levels of teb are as effective as higher levels for stimulating full activity.

Figure 4:
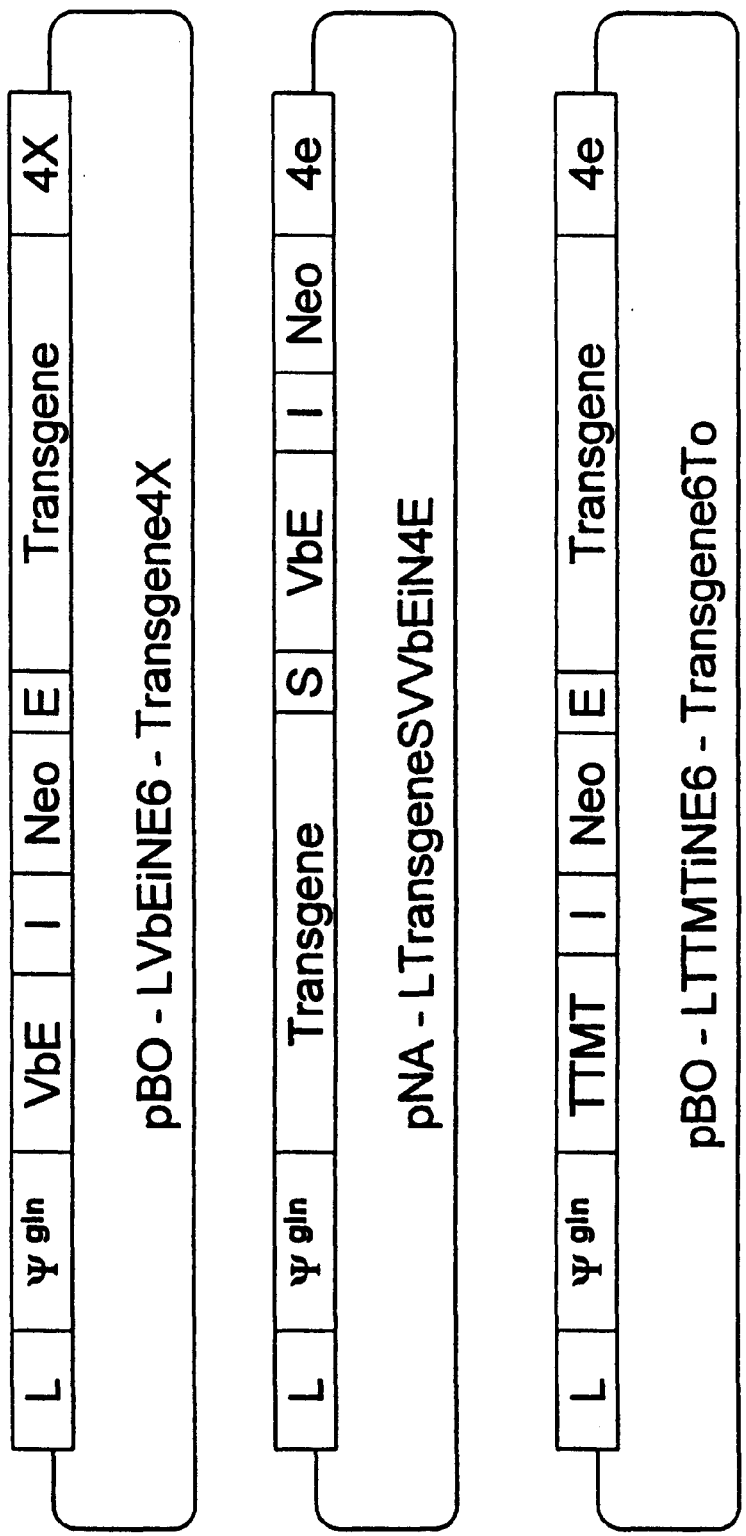

FIG. 4 is a schematic drawing of representative single-plasmid constructs involving VbR use.

Figure 5:
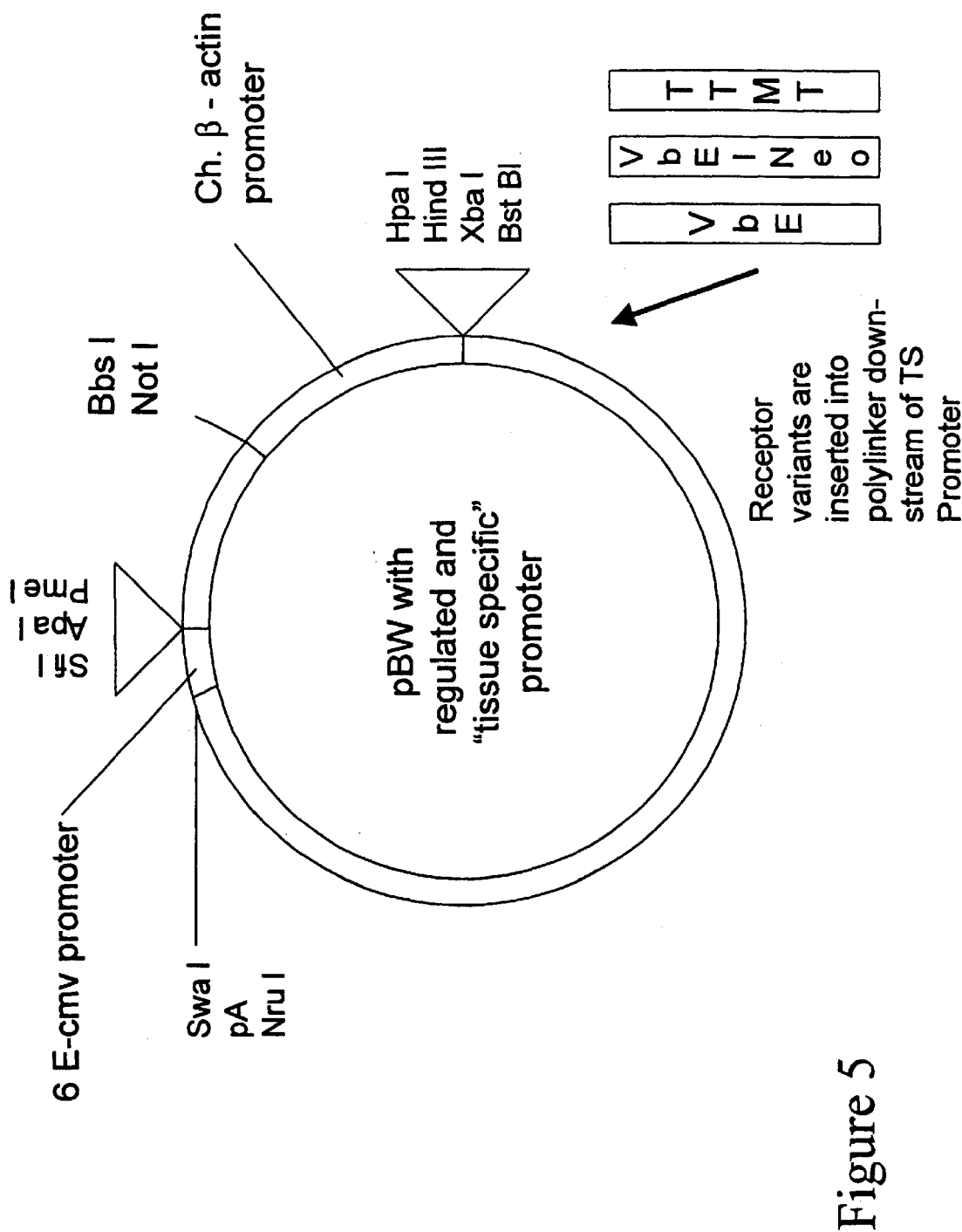

FIG. 5 illustrates the construction of the pBW plasmid.

DETAILED DESCRIPTION OF THE INVENTION

In accordance with the present invention, there are provided method(s) for modulating the transcription of exogenous nucleic acid(s) in a host containing:

(i) a nucleic acid construct comprising a promoter and said exogenous nucleic acid(s) under the control of a regulatory element; and (ii) a receptor peptide comprising a DNA binding domain, and the ligand binding domain and hinge region of a non-mammalian member of the nuclear receptor superfamily which is not normally present in the cells of said host, wherein said receptor peptide activates said regulatory element in the absence of an exogenous dimer partner therefor and in the presence of a ligand for said ligand binding domain, said method comprising administering to said host an amount of ligand effective to modulate the transcription of said exogenous nucleic acid(s); wherein ligand is not normally present in the cells of said host.

As employed herein, the terms "modulate" and "modulating" refer to the ability of a given ligand/receptor peptide complex to activate/deactivate and/or up-regulate/down-regulate transcription of exogenous nucleic acids, relative to the transactivation activity of said receptor peptide in the absence of ligand. The actual effect of complex formation on the transactivation activity of a receptor peptide will vary depending on the specific ligand and DNA binding domains employed in the receptor peptide and on the regulatory element with which the ligand/receptor peptide complex interacts.

As employed herein, the term "host" refers to the cell, tissue, organ or organism in need of transcriptional regulation of exogenous or endogenous nucleic acids. Preferably, hosts are mammalian or mammalian derived cells or tissue. Exemplary mammals include: humans; domesticated animals, e.g., rat, mouse, rabbit, canine, and feline; farm animals, e.g., chicken, bovine, porcine and ovine; and animals of zoological interest, e.g., monkey and baboon; and the like.

As employed herein, a "dimer partner" refers to members of the nuclear receptor superfamily to which other members preferentially bind to form heterodimeric species. For example, members of the nuclear receptor superfamily preferentially form heterodimers with a common partner, the retinoid X (or 9-cis retinoic acid) receptor (RXR, see, for example, Yu et al. (1991) *Cell* 67:1251–1266; Bugge et al. (1992) *EMBO J.* 11:1409–1418; Kliewer et al. (1992) *Nature* 355:446–449; Leid et al, (1992) *Cell* 68:377–395; Marks et al. (1992) *EMBO J.* 11:1419–1435; Zhang et al. (1992) *Nature* 355:441–446; Issemann et al. (1993) *Biochimie.* 75:251–256). Additional dimer partners for members of the nuclear receptor superfamily include ultraspiracle (Usp), farnesoid X receptor (FXR), and the like.

Receptor peptides utilized in the present invention are characterized as being fully functional in mammalian cells without the addition of any exogenous dimer partners therefor. For such receptor peptides, the presence of endogenous dimer partner is sufficient to promote transcription. As employed herein, the phrase "exogenous dimer partner" refers to a dimer partner for the receptor peptide that must be introduced into the host, as opposed to endogenous dimer partner(s), i.e., dimer partners which are native to the unmodified host.

In accordance with a particular aspect of the invention, it has been discovered that the hinge region, bounded by the ligand binding domain and DNA binding domain of the native *Bombyx mori* receptor, enables receptor peptides to function in the absence of exogenous dimer partners. Specifically, about 27 amino acid residues (i.e. amino acid residues 273–299, as set forth in SEQ ID NO:2, in the hinge region of bR) are sufficient to confer high affinity for complex formation with endogenous dimer partner. In accordance with a preferred embodiment of the present invention, the hinge region of a non-mammalian member of the nuclear receptor superfamily can be characterized as any sequence having substantial sequence identity with amino acid residues 273–362 set forth in SEQ ID NO:3, or substantial portions thereof which confer sufficiently high affinity for endogenous dimer partner (i.e., the amino acid residues 273–299 set forth in SEQ ID NO:3). In the most preferred embodiment, hinge amino acids which are the same as residues 273–362, as set forth in SEQ ID NO:3, will not be modified or altered in order to retain the binding characteristics contemplated by the present invention.

The hinge region can be functionally located in either orientation and at various positions within the receptor peptide. For example, the hinge region can be positioned at either the amino or carboxy terminus of the receptor peptide, or therebetween. In a preferred embodiment of the present invention, the hinge region is positioned internally between the ligand binding and DNA binding domains of the receptor peptide (see FIG. 1A).

As employed herein, the phrase "ligand binding domain of a non-mammalian member of the nuclear receptor superfamily, which is not normally present in the cells of said host" refers to ligand binding domains derived from receptors which are not endogenous to the host. Members of the nuclear receptor superfamily are characterized by the presence of five domains: A/B, C, D, E and F (Evans, R. *Science* 240:889–895 (1988)), wherein "E" corresponds to the ligand binding domain. Ligand binding domains which are not endogenous to a host include ligand binding domains which are modified to be non-responsive to ligands endogenous or native to the host. Ligand binding domains contemplated for use according to the present invention can be derived from non-mammalian member(s) of the nuclear receptor superfamily which members are not normally present in the cells of a host. Ligand binding domains are preferably derived from the carboxy-terminal portion of non-mammalian receptors which are capable of activating transcription of regulatory elements in the absence of exogenous dimer partner therefore. Exemplary receptors which are not normally present in mammalian cells include insect receptors, plant receptors, and the like.

Exemplary ligand binding domains derived from insect receptors include those derived from lepidopteran species such as *Bombyx mori*, (Swevers et al. *Insect Biochem. Molec. Biol.* 25(7):857–866 (1995)), *Choristoneura fumiferana* (Palli et al. *Insect Biochem. Molec. Biol.* 26(5): 485–499 (1996)), *Manduca sexta* (Fujiwara et al. *Insect Biochem. Molec. Biol.* 25(7):845–856 (1995)), *Aedes aegypti* (Cho et al. *Insect Biochem Molec. Biol.* 25:19–27 (1995), *Chorinomus tentans* (Imhof et al. *Insect Biochem.*

*Molec. Biol.* 25:115–124 (1993), and the like. Presently preferred insect receptors from which the ligand binding domain is derived substantially lack the C-terminal "F" domain, thereby providing an intact protein that is less than about 700 amino acids. Preferred sequences encoding receptors utilized in the present invention are those nucleic acid sequences which have substantial sequence identity with the sequence set forth in SEQ ID NO:2. Nucleic acids having the sequence set forth in SEQ ID NO:2 are presently most preferred.

In addition, the ligand binding domains of insect receptors contemplated for use in the present invention preferably share less than 80% sequence identity with the ligand binding domain of Drosophila melanogaster ecdysone receptor. Further, such ligand binding domains are preferably characterized as being sensitive to non-steroidal compounds, such as diacyl hydrazines.

Ligand binding domains can be functionally located in either orientation and at various positions within the receptor peptide. For example, the ligand binding domain can be positioned at either the amino or carboxy terminus of the receptor peptide, or therebetween. In a preferred embodiment of the present invention, the ligand binding domain is positioned at the carboxy terminus of the receptor peptide (see FIG. 1A).

Exemplary ligand binding domains can alternatively be characterized as comprising substantial sequence identity with amino acid residues 263–586 set forth in SEQ ID NO:3, or substantial portions thereof (i.e., typically at least 46 or more contiguous nucleotides thereof). Modifications of this sequence contemplated for use in the practice of the present invention include replacing several amino acids of the ligand binding domain with sequences from ligand binding domains of other members of the nuclear receptor superfamily, such as retinoic acid receptor and thyroid hormone receptor (FIG. 1B). These modifications provide unique transactivating characteristics and/or eliminate restriction sites, which facilitate the construction of useful peptide-based viral constructs.

DNA-binding domains contemplated for use in the preparation of invention receptor peptides are typically obtained from DNA-binding proteins (e.g., transcription factors). The term "DNA-binding domain" is understood in the art to refer to an amino acid sequence that is able to bind to DNA. As used herein, the term "DNA-binding domain" encompasses a minimal peptide sequence of a DNA-binding protein up to the entire length of a DNA-binding protein, so long as the DNA-binding domain functions to associate with a particular regulatory element.

DNA-binding domains are known to function heterologously in combination with other functional domains by maintaining the ability to bind the natural DNA recognition sequence (see, e.g., Brent and Ptashne, (1985) *Cell*, 43:729–736). For example, with respect to hormone receptors, DNA-binding domains are interchangeable, thereby providing numerous chimeric receptor proteins (see, e.g., U.S. Pat. No. 4,981,784; and Evans, R., (1988) *Science*, 240:889–895). Similar to the ligand binding domain, the DNA-binding domain can be positioned at either the carboxy terminus or the amino terminus, or the DNA-binding domain can be positioned between the ligand binding domain and the activation domain. In preferred embodiments of the present invention, the DNA-binding domain is positioned internally between the ligand binding domain and the activation domain.

"DNA-binding protein(s)" contemplated for use herein belong to the well-known class of proteins that are able to directly bind DNA and facilitate initiation or repression of transcription. Exemplary DNA-binding proteins contemplated for use herein include transcription control proteins (e.g., transcription factors and the like; Conaway and Conaway, 1994, "Transcription Mechanisms and Regulation", *Raven Press Series on Molecular and Cellular Biology*, Vol. 3, Raven Press, Ltd., New York, N.Y.).

Transcription factors contemplated for use herein as a source of such DNA binding domains include, e.g., homeobox proteins, zinc finger proteins, hormone receptors, helix-turn-helix proteins, helix-loop-helix proteins, basic-Zip proteins (bzip), β-ribbon factors, and the like. See, for example, Harrison, S., "A Structural Taxonomy of DNA-binding Domains," *Nature*, 353:715–719. Homeobox DNA-binding proteins suitable for use herein include, for example, HOX, STF-1 (Leonard et al., 1993, *Mol. Endo.*, 7:1275–1283), Antp, Mat α-2, INV, and the like. See, also, Scott et al. (1989), *Biochem. Biophys. Acta*, 989:25–48. It has been found that a fragment of 76 amino acids (corresponding to amino acids 140–215 described in Leonard et al., (1993) *Mol. Endo.*, 7:1275–1283) containing the STF-1 homeodomain binds DNA as tightly as wild-type STF-1. Suitable zinc finger DNA-binding proteins for use herein include Zif268, GLI, XFin, and the like. See also, Klug and Rhodes (1987) *Trends Biochem. Sci.*, 12:464; Jacobs and Michaels (1990) *New Biol.*, 2:583; and Jacobs (1992), *EMBO J.*, 11:4507–4517.

An additional DNA binding domain contemplated for use in the practice of the present invention is the GAL4 DNA binding domain. The DNA binding domain of the yeast GAL4 protein comprises at least the first 74 amino terminal amino acids thereof (see, for example, Keegan et al., *Science* 231:699–704 (1986)). Preferably, the first 90 or more amino terminal amino acids of the GAL4 protein will be used, with the 147 amino terminal amino acid residues of yeast GAL4 being presently most preferred.

Preferably, DNA-binding domain(s) used herein is(are) obtained from a member of the nuclear receptor superfamily. As used herein, the phrase "member(s) of the nuclear receptor superfamily" (also known as "intracellular receptors" or "steroid/thyroid hormone superfamily of receptors") refers to hormone binding proteins that operate as ligand-dependent transcription factors, including identified members of the nuclear receptor superfamily for which specific ligands have not yet been identified (referred to hereinafter as "orphan receptors").

Exemplary members of the nuclear receptor superfamily (including the various isoforms thereof) include steroid receptors such as glucocorticoid receptor (GR), mineralocorticoid receptor (MR), estrogen receptor (ER), progesterone receptor (PR), androgen receptor (AR), vitamin $D_3$ receptor (VDR), and the like; plus retinoid receptors, such as the various isoforms of retinoic acid receptor (e.g., RARα, RARβ, or RARγ), the various isoforms of retinoid X receptor (e.g., RXRα, RXRβ, or RXRγ), and the like (see, e.g., U.S. Pat. Nos. 4,981,784; 5,171,671; and 5,071,773); thyroid receptors (TR), such as TRα, TRβ, and the like; insect derived receptors such as the ecdysone receptor, and the like; as well as other gene products which, by their structure and properties, are considered to be members of the superfamily, as defined hereinabove, including the various isoforms thereof. Examples of orphan receptors contemplated for use herein as a source of DNA binding domains include HNF4 [see, for example, Sladek et al., in *Genes & Development* 4: 2353–2365 (1990)], the COUP family of receptors [see, for example, Miyajima et al., in *NAR* 16: 11057–11074 (1988), and Wang et al., in *Nature* 340: 163–166 (1989)], COUPlike receptors and COUP homologs, such as those described by Mlodzik et al., in *Cell* 60: 211–224 (1990) and Ladias et al., in *Science* 251: 561–565 (1991), various isoforms of peroxisome proliferator-activated receptors (PPARs; see, for example, Issemann and Green, supra), the insect derived knirps and knirps-related receptors, and the like.

The DNA-binding domains of all members of the nuclear receptor superfamily are related. Such domains consist of 66–68 amino acid residues, and possess about 20 invariant amino acid residues, including nine cysteines. Members of the superfamily are characterized as proteins which contain these 20 invariant amino acid residues. The highly conserved amino acids of the DNA-binding domain of members of the superfamily are as follows:

Cys - X - X - Cys - X - X - Asp* - X -
Ala* - X - Gly* - X - Tyr* - X - X -
X - X - Cys - X - X - Cys - Lys* - X -
Phe - Phe - X - Arg* - X - X - X - X -
X - X - X - X - X - (X - X -) Cys - X -
X - X - X - X - (X - X - X -) Cys - X -
X - X - Lys - X - X - Arg - X - X -
Cys - X - X - Cys - Arg* - X - X -
Lys* - Cys - X - X - X - Gly* - Met
(SEQ ID NO:1)

wherein X designates non-conserved amino acids within the DNA-binding domain; an asterisk denotes the amino acid residues which are almost universally conserved, but for which variations have been found in some identified hormone receptors; and the residues enclosed in parenthesis are optional residues (thus, the DNA-binding domain is a minimum of 66 amino acids in length, but can contain several additional residues).

As used herein, the phrase "substantial sequence identity" refers to nucleotide sequences which share at least about 80% identity with respect to a reference sequence, and amino acid sequences which typically share more than 90% amino acid identity, regardless of the algorithm used to determine sequence identity. It is recognized, however, that proteins (and DNA or mRNA encoding such proteins) containing less than the above-described level of homology produced as splice variants or as a result of conservative amino acid substitutions (or substitution of degenerate codons) are contemplated to be within the scope of the present invention.

The phrase "substantially the same," used in reference to a DNA nucleotide sequence, an RNA ribonucleotide sequence, or an amino acid sequence, refers to sequences that have slight and non-consequential sequence variations from the actual sequences disclosed herein. Species that are substantially the same are considered to be equivalent to the disclosed sequences. In this regard, "slight and non-consequential sequence variations" mean that sequences that are substantially the same as the DNA, RNA, or proteins disclosed and claimed herein are functionally equivalent to the sequences disclosed and claimed herein. Functionally equivalent sequences will function in substantially the same manner to produce substantially the same effect as the sequences disclosed.

Receptor peptides employed in the present invention can be modified by the introduction of activation domains. Activation domains contemplated for use in the practice of the present invention are well known in the art and can readily be identified by those of skill in the art. Activation domains contemplated for use herein are typically derived from transcription factors and comprise a contiguous sequence that functions to activate gene expression when associated with a suitable DNA-binding domain and a suitable ligand binding domain. An activation domain can be positioned at any convenient site within the receptor peptide, i.e., at the carboxy terminus, the amino terminus or between the ligand binding domain and the DNA binding domain. In preferred embodiments of the present invention, the activation domain is positioned at the amino terminus of the receptor peptide.

Suitable activation domains can be obtained from a variety of sources, e.g., from the N-terminal region of members of the nuclear receptor superfamily, from transcription factor activation domains, such as, for example, VP16, GAL4, NF-kB or BP64 activation domains, and the like. The presently most preferred activation domain contemplated for use in the practice of the present invention is obtained from the C-terminal region of the VP16 protein.

As employed herein, the term "ligand" (or ligand precursor) refers to a non-steroidal substance or compound which, in its native state (or after conversion to its "active" form), binds to the receptor peptide, thereby creating a ligand/receptor peptide complex, which in turn can bind an appropriate response element and activate transcription therefrom. Ligands function to modulate transcription of nucleic acid(s) maintained under the control of a response element. In accordance with one aspect of the present invention, unless and until a suitable ligand is administered to the host, substantially no transcription of the desired exogenous nucleic acids occurs.

Preferred ligands contemplated for use in the practice of the present invention are ligands characterized as not normally present in the cells of the host to be treated. Such ligands are referred to as being exogenous to the host. An example of a class of ligands not naturally present in mammalian systems are compounds referred to as hydrazines, preferably diacyl hydrazines.

Hydrazines contemplated for use in the present invention include compounds which are readily available and are/or relatively inexpensive to manufacture. One such compound, tebufenozide, is a non-steroidal ecdysone agonist which is used commercially as an insecticide. This compound specifically targets lepidopteran species, including *Bombyx mori*. Tebufenozide has undergone extensive testing in animal hosts and has proved to be of very low toxicity to mammals and other non-insect species.

Exemplary hydrazines contemplated for use herein include 1,2-diacyl hydrazines (e.g., tebufenozide), N'-substituted-N,N'-disubstituted hydrazines, dibenzoylalkyl cyanohydrazines, N-substituted-N-alkyl-N,N-diaroyl hydrazines, N-substituted-N-acyl-N-alkyls, carbonyl hydrazines, N-aroyl-N'-alkyl-N'-aroyl hydrazines, and the like.

Ligands are administered in a manner compatible with the route of administration, the dosage formulation, and in a therapeutically effective amount. The required dosage will vary with the particular treatment desired, the degree and duration of therapeutic effect desired, the judgment of the practitioner, as well as properties peculiar to each individual. Moreover, suitable dosage ranges for systemic application depend on the route of administration. It is anticipated that dosages between about 10 micrograms and about 1 milligram per kilogram of body weight per day will be used for therapeutic treatment.

An effective amount of ligand contemplated for use in the practice of the present invention is the amount of ligand (e.g., diacyl hydrazine(s)) required to achieve the desired level of transcription and/or translation of exogenous nucleic acid. A therapeutically effective amount is typically an amount of a ligand or ligand precursor that, when administered in a physiologically acceptable composition, is sufficient to achieve a plasma concentration of the transcribed or expressed nucleic acid product from about 0.1 µg/ml to about 100 µg/ml, preferably from about 1.0 µg/ml to about 50 µg/ml, more preferably at least about 2 µg/ml and usually 5 to 10 µg/ml.

Ligand can be administered in a variety of ways, as are well-known in the art, i.e., by any means that produces contact between ligand and receptor peptide. For example, such ligands can be administered topically, orally, intravenously, intraperitoneally, intravascularly, and the like. The administration can be by any conventional means available for use in conjunction with pharmaceuticals, e.g., by intravenous injection; either as individual therapeutically active ingredients or in a combination with other therapeutically active ingredients. Ligands contemplated for use in the practice of the present invention can be administered alone, but are generally administered with a pharmaceutical carrier selected on the basis of the chosen route of administration and standard pharmaceutical practice.

Therapeutic compositions containing suitable ligand are preferably administered intravenously, as by injection of a unit dose, for example. The term "unit dose," when used in reference to a therapeutic composition of the present invention, refers to a quantity of ligand suitable as unitary dosage for the subject, each unit containing a predetermined quantity of active material calculated to produce the desired therapeutic effect in association with the required diluent, i.e., carrier, or vehicle. It may be particularly advantageous to administer such compounds in depot or long-lasting form as discussed hereinafter.

Suitable regimes for initial administration and booster shots are variable, but are typified by an initial administration followed by repeated doses at one or more intervals by a subsequent injection or other administration. Alternatively, continuous intravenous infusion sufficient to maintain concentrations in the blood in the ranges specified for in vivo therapies are contemplated.

Since it has been previously reported that the above-described diacyl hydrazines are neither toxic, teratogenic, nor known to affect mammalian physiology, they are ideal candidates for use as inducers in cultured cells and transgenic mammals according to invention methods.

Certain nucleic acid constructs contemplated for use in one aspect of the present invention include promoters and regulatory elements operatively associated with exogenous nucleic acids. In a preferred embodiment of the present invention, receptor peptide, in the presence of a ligand therefor, binds the regulatory element and activates transcription of the exogenous nucleic acids.

Regulatory elements contemplated for use in the practice of the present invention include elements responsive to the invention receptor peptide. In a preferred embodiment of the present invention, such elements are exogenous regulatory elements not normally present in the cells of the host. One class of exogenous regulatory elements contemplated for use herein includes hormone response elements which modulate transcription of exogenous nucleic acid when bound to the DNA binding domain of an invention receptor peptide.

Additional regulatory elements that may be utilized in the present invention include exogenous regulatory elements responsive to a non-mammalian transactivator. One such transactivator-responsive regulatory element is an operator which confers responsiveness to antibiotics. Exemplary operators contemplated for use in this aspect of the invention include the tetracycline-analog regulated operator, the TET operator, the Lac operator, and the like.

Exogenous response elements contemplated for use herein are short cis-acting sequences (i.e., having about 12–20 bp) that are required for activation of transcription in response to association with a suitable ligand, such as diacyl hydrazines, and an invention receptor peptide. Response element sequences contemplated for use herein function in a position- and orientation-independent fashion. Exemplary response elements include hormone response elements, GAL4 response elements and the like.

Hormone response elements contemplated for use in the present invention are response elements which are responsive to members of the nuclear receptor superfamily. These response elements comprise at least two half-sites (in either direct repeat or inverted repeat orientation to one another), separated by a spacer of 0–5 nucleotides. As used herein, the term "half-site" refers to a contiguous 6 nucleotide sequence that is bound by a particular member of the nuclear receptor superfamily. Typically, two half-sites with a corresponding spacer make up a hormone response element. Hormone response elements can be incorporated in multiple copies into various transcription regulatory regions.

Preferred hormone response elements employed in the practice of the present invention comprise a first half-site and a second half-site, separated by a spacer of 0–5 nucleotides;

wherein each half-site has the sequence:
-RGBNNM-,
(or complements thereof) wherein
each R is independently selected from A or G;
each B is independently selected from G, C, or T;
each N is independently selected from A, T, C, or G; and
each M is independently selected from A or C; with the proviso that at least 4 nucleotides of each -RGBNNM- group of nucleotides are identical with the nucleotides at comparable positions of the sequence -AGGTCA-.

Exemplary half-sites having the -RGBNNM- motif for use in preparing response elements useful in the practice of the present invention include, for example, half-sites selected from -AGGGCA-, -AGTTCA-, -AGGTAA-, -AGGTCA-, -GGTTCA-, -GGGTTA-, -GGGTGA-, -AGGTGA-, -GGGTCA-, and the like. A particularly preferred first half-site is -AGTGCA-.

Additional response elements included the GAL4 response element. Exemplary GAL4 response elements are those containing the palindromic 17-mer:

5'-CGGAGGACTGTCCTCCG-3' (SEQ ID NO:4),
such as, for example, 17 MX, as described by Webster et al., in Cell 52:169–178 (1988), as well as derivatives thereof. Additional examples of suitable response elements include those described by Hollenberg and Evans in *Cell* 55:899–906 (1988); or Webster et al. in *Cell* 54:199–207 (1988).

Regulatory elements employed in the practice of the present invention are operably linked to a suitable promoter for transcription of exogenous nucleic acid(s) product(s). As used herein, the term "promoter" refers to a specific nucleotide sequence recognized by RNA polymerase, the enzyme that initiates RNA synthesis. The promoter sequence is the site at which transcription can be specifically initiated under proper conditions. When exogenous nucleic acid(s), operatively linked to a suitable promoter, is(are) introduced into the cells of a suitable host, expression of the exogenous nucleic acid(s) is(are) controlled by the presence of ligands, which are not normally present in the host cells.

Promoters contemplated for control of expression of exogenous nucleic acids employed in the practice of the present invention include inducible (e.g., minimal CMV promoter, minimal TK promoter, modified MMLV LTR), constitutive (e.g., chicken b-actin promoter, MMLV LTR (non-modified), DHFR), and/or tissue specific promoters.

Inducible promoters contemplated for use in the practice of the present invention comprise transcription regulatory regions that function maximally to promote transcription of mRNA under inducing conditions. Examples of suitable inducible promoters include DNA sequences corresponding to: the E. coli lac operator responsive to IPTG (see Nakamura et al., Cell, 18:1109–1117, 1979); the metallothionein promoter metal-regulatory-elements responsive to heavy-metal (e.g., zinc) induction (see Evans et al., U.S. Pat. No. 4,870,009), the phage T7lac promoter responsive to IPTG (see Studier et al., Meth. Enzymol., 185: 60–89, 1990; and U.S. Pat. No. 4,952,496), the heat-shock promoter; the TK minimal promoter; the CMV minimal promoter; a synthetic promoter; and the like.

Exemplary constitutive promoters contemplated for use in the practice of the present invention include the CMV promoter, the SV40 promoter, the DHFR promoter, the mouse mammary tumor virus (MMTV) steroid-inducible promoter, Moloney murine leukemia virus (MMLV) promoter, elongation factor 1α (EF1α) promoter, albumin promoter, APO A1 promoter, cyclic AMP dependent kinase II (CaMKII) promoter, keratin promoter, CD3 promoter, immunoglobulin light or heavy chain promoters, neurofiliment promoter, neuron specific enolase promoter, L7 promoter, CD2 promoter, myosin light chain kinase promoter, HOX gene promoter, thymidine kinase (TK) promoter, RNA Pol II promoter, MYOD promoter, MYF5 promoter, phophoglycerokinase (PGK) promoter, Stf1 promoter, Low Density Lipoprotein (LDL) promoter, chicken b-actin promoter (used in conjunction with ecdysone response element) and the like.

As readily understood by those of skill in the art, the term "tissue specific" refers to the substantially exclusive initiation of transcription in the tissue from which a particular promoter, which drives expression of a given gene, is derived (e.g., expressed only in T-cells, endothelial cells, smooth muscle cells, and the like). Exemplary tissue specific promoters contemplated for use in the practice of the present invention include the GH promoter, the NSE promoter, the GFAP promoter, neurotransmitter promoters (e.g., tyrosine hydroxylase, TH, choline acetyltransferase, ChAT, and the like), promoters for neurotropic factors (e.g., a nerve growth factor promoter, NT-3, BDNF promoters, and the like), and so on.

As used herein, when referring to nucleic acids, the phrase "exogenous to said mammalian host" or simply "exogenous" refers to nucleic acids not naturally found at levels sufficient to provide a function in the particular cell where transcription is desired. For example, exogenous nucleic acids can be either natural or synthetic nucleic acids, which are introduced into the host in the form of DNA or RNA. The nucleic acids of interest can be introduced into target cells (for in vitro applications), or the nucleic acids of interest can be introduced directly or indirectly into a host by the transfer of transformed cells into a host.

In contrast to exogenous nucleic acids, the phrase "endogenous nucleic acids" or "endogenous genes" refers to nucleic acids naturally found at levels sufficient to provide a function in the particular cell where transcription is desired Exogenous nucleic acids contemplated for use in the practice of the present invention include wild type and/or therapeutic nucleic acids.

"Wild type" genes are those that are native to cells of a particular type. Exemplary wild type nucleic acids are genes which encode products:
   the substantial absence of which leads to the occurrence of a non-normal state in a host; or
   a substantial excess of which leads to the occurrence of a non-normal state in a host.

Such genes may not be expressed in biologically significant levels or may be undesirably overexpressed, respectively. Thus, for example, while a synthetic or natural gene coding for human insulin would be exogenous genetic material to a yeast cell (since yeast cells do not naturally contain insulin genes), a human insulin gene inserted into a human skin fibroblast cell would be a wild type gene with respect to the fibroblast since human skin fibroblasts contain genetic material encoding human insulin, although human skin fibroblasts do not express human insulin in biologically significant levels.

Therapeutic nucleic acids contemplated for use in the practice of the present invention include those which:
   encode products which are toxic to the cells in which they are expressed; or
   encode products which impart a beneficial property to a host; or
those which transcribe nucleic acids which modulate transcription and/or translation of endogenous genes.

As employed herein, the phrase "therapeutic nucleic acids" refers to nucleic acids which impart a beneficial function to the host in which such nucleic acids are transcribed. Therapeutic nucleic acids are those that are not naturally found in host cells. For example, synthetic or natural nucleic acids coding for wild type human insulin would be therapeutic when inserted into a skin fibroblast cell so as to be expressed in a human host, where the human host is not otherwise capable of expressing functionally active human insulin in biologically significant levels. Further examples of therapeutic nucleic acids include nucleic acids which transcribe antisense constructs used to suppress the expression of endogenous genes. Such antisense transcripts bind endogenous nucleic acid (mRNA or DNA) and effectively cancel out the expression of the gene. In accordance with the methods described herein, therapeutic nucleic acids are expressed at a level that provides a therapeutically effective amount of the corresponding therapeutic protein.

Exogenous nucleic acids useful in the practice of the present invention include genes that encode biologically active proteins of interest, such as, e.g., secretory proteins that can be released from said cell; enzymes that can metabolize a toxic substance to produce a non-toxic substance, or that metabolize an inactive substance to produce a useful substance; regulatory proteins; cell surface receptors; and the like. Useful genes include genes that encode blood clotting factors such as human factors VIII and IX; genes that encode hormones such as insulin, parathyroid hormone, luteinizing hormone releasing factor (LHRH), alpha and beta seminal inhibins, and human growth hormone; genes that encode proteins such as enzymes, the absence of which leads to the occurrence of an abnormal state; genes encoding cytokines or lymphokines such as interferons, granulocytic macrophage colony stimulating factor (GM-CSF), colony stimulating factor-1 (CSF-1), tumor necrosis factor (TNF), and erythropoietin (EPO); genes encoding inhibitor substances such as alpha$_1$-antitrypsin; genes encoding substances that function as drugs, e.g., genes encoding the diphtheria and cholera toxins; and the like.

Additional nucleic acids contemplated for use in accordance with the present invention include genes which encode proteins present in dopaminergic neurons (useful, for example, for the treatment of Parkinson's disease), cholinergic neurons (useful, for example, for the treatment of Alzheimer's disease), hippocampal pyramidal neurons (also useful for the treatment of Alzheimer's disease), norepinephrine neurons (useful, for example, for the treatment of epilepsy), spinal neurons (useful, for example, for the treatment of spinal injury), glutamatergic neurons (useful, for example, for the treatment of schizophrenia), cortical neurons (useful, for example, for the treatment of stroke and brain injury), motor and sensory neurons (useful, for example, for the treatment of amyotrophic lateral sclerosis), and the like.

Typically, nucleic acid sequence information for proteins encoded by exogenous nucleic acid(s) contemplated for use employed herein can be located in one of many public access databases, e.g., GENBANK, EMBL, Swiss-Prot, and PIR, or in related journal publications. Thus, those of skill in the art have access to sequence information for virtually all known genes. Those of skill in the art can either obtain the corresponding nucleic acid molecule directly from a public depository or the institution that published the sequence. Optionally, once the nucleic acid sequence encoding a desired protein has been ascertained, the skilled artisan can employ routine methods, e.g., polymerase chain reaction (PCR) amplification, to isolate the desired nucleic acid molecule from the appropriate nucleic acid library. Thus, all known nucleic acids encoding proteins of interest are available for use in the methods and products described herein.

Additional components which can optionally be incorporated into invention constructs include selectable markers and genes encoding proteins required for retroviral packaging, e.g., the pol gene, the gag gene and the env gene.

Selectable markers contemplated for use in the practice of the present invention include antibiotic resistance genes, genes which enable cells to process metabolic intermediaries, and the like. Exemplary antibiotic resistance genes include genes which impart tetracycline resistance, genes which impart ampicillin resistance, neomycin resistance, hygromycin resistance, puromycin resistance, and the like.

Genes which enable cells to process metabolic intermediaries include genes which permit cells to incorporate L-histidinol, genes encoding thymidine kinase, genes encoding xanthine-guanine phosphoribosyl transferase (gpt), genes encoding dihydrofolate reductase, genes encoding asparagine synthetase, and the like.

In accordance with a preferred embodiment of the present invention, the host further comprises, in addition to the receptor peptide, a non-mammalian transactivator, not a member of the nuclear receptor superfamily and not normally present in the cells of said host, and a compatible transactivator responsive regulatory element not normally present in cells of said host. The transactivator responsive regulatory element controls transcription of the exogenous nucleic acid(s) or a second nucleic acid construct comprising a second exogenous nucleic acid(s). Examples of transactivator responsive regulatory elements include operators which are responsive to non-mammalian transactivators which confer responsiveness to antibiotics. Exemplary operators contemplated for use in this aspect of the invention include the tetracycline-analog regulated operator, the TET operator, the Lac operator, and the like. Preferably, the transactivator responsive regulatory elements employed in the practice of the present invention are operably linked to a suitable promoter for transcription of exogenous nucleic acid(s) proteins.

Non-mammalian transactivators, other than members of the nuclear receptor superfamily, contemplated for use in the practice of the present invention function in the absence of exogenous dimer partner. Examples of transactivators that typically function in the absence of exogenous dimer partner are tetracycline-controlled transactivators, Vp16-Lac fusion transactivators, and the like. When contained as part of a transactivating construct, the transactivator can be positioned at any convenient site within the construct, i.e. at the carboxy terminus or the amino terminus of the transactivating construct. In preferred embodiments of present invention, the transactivator is positioned at the amino terminus of the transactivating construct (FIG. 1C).

Preferably, the non-mammalian transactivator confers responsiveness to antibiotics. An example of a non-mammalian transactivator which confers responsiveness to antibiotics, as contemplated for use in the practice of the present invention is the tetracycline-controlled transactivator. The tetracycline inducible system is well-known in the art (see, e.g, Gossen et al. (1992) *PNAS* 89, 5547–5551; Gossen et al. (1993) *TIBS* 18, 471–475; Furth et al. (1994) *PNAS* 91, 9302–9306; Shockett et al. (1995) *PNAS* 92, 6522–6526; and Hoshimaru et al. (1996) *PNAS* 93(4): 1518–1523). Other examples of non-mammalian transactivators well known in the art include the IPTG inducible system based on a VP16-Lac repressor fusion which functions through lac operator sequences inserted into heterologous promoters (see, e.g., Baim et al. (1991) *PNAS* 88:5072–5076).

In addition to the receptors/transactivators set forth above, those of skill in the art recognize that other transactivators can be used herein, e.g., homeobox proteins, zinc finger proteins, hormone receptors, helix-turn-helix proteins, helix-loop-helix proteins, basic-Zip proteins (bzip), β-ribbon factors, and the like. See, for example, Harrison, S., "A Structural Taxonomy of DNA-binding Domains," *Nature*, 353:715–719. Homeobox DNA-binding proteins suitable for use herein include, for example, HOX, STF-1 (Leonard et al., (1993) *Mol. Endo.*, 7:1275–1283), Antp, Mat α-2, INV, and the like. See, also, Scott et al. (1989) *Biochem. Biophys. Acta*, 989:25–48. It has been found that a fragment of 76 amino acids (corresponding to amino acids 140–215 described in Leonard et al., (1993) *Mol. Endo.*, 7:1275–1283) containing the STF-1 homeodomain binds DNA as tightly as wild-type STF-1. Suitable zinc finger DNA-binding proteins for use herein include Zif268, GLI, XFin, and the like. See also, Klug and Rhodes (1987) *Trends Biochem. Sci.*, 12:464; Jacobs and Michaels (1990) *New Biol.*, 2:583; and Jacobs (1992) *EMBO J.*, 11:4507–4517.

In accordance with a still further embodiment of the present invention, there are provided methods for producing transgenic animals capable of prolonged and regulated expression of exogenous nucleic acid(s), said method comprising introducing into early-stage embryos or stem cells:
  (i) a nucleic acid construct comprising a promoter and said exogenous nucleic acid(s) under the control of a regulatory element;
  (ii) nucleic acid encoding a receptor peptide comprising a DNA binding domain, and the ligand binding domain and hinge region of a non-mammalian member of the nuclear receptor superfamily which is not normally present in the cells of said host, wherein said receptor peptide activates said regulatory element in the absence of an exogenous dimer partner therefor and in the presence of a ligand for said ligand binding domain.

As used herein, the phrase "transgenic animal" refers to an animal that contains one or more inheritable expression constructs containing one or more exogenous nucleic acid(s) under the transcription control of an operator and/or hormone response element as described herein.

Methods of making transgenic animals using a particular nucleic acid construct are well-known in the art. When preparing invention transgenic animals, it is preferred that two transgenic lines are generated. The first line will express, for example, a receptor peptide as described above (e.g., VbR). Tissue specificity is conferred by the selection of a tissue-specific promoter (e.g., T-cell specific) that will direct expression of the receptor peptide to appropriate tissue. A second line contains a nucleic acid construct comprising a promoter and exogenous nucleic acid under the control of a regulatory element.

In a presently preferred embodiment, an invention transgenic animal contains one or more expression constructs containing nucleic acid encoding receptor peptide and exogenous nucleic acid under the transcription control of a regulatory element. Thus, with tissue specific expression of the receptor peptide as described above and timely hormone treatment, inducible gene expression can be achieved with spatial, dosage, and temporal specificity.

In yet another embodiment of the present invention, there are provided methods of inducing the transcription of an exogenous nucleic acid(s) in a host containing:

(i) a nucleic acid construct comprising a promoter and said exogenous nucleic acid(s) under the control of a regulatory element;

(ii) nucleic acid encoding a receptor peptide comprising a DNA binding domain, and the ligand binding domain and hinge region of a non-mammalian member of the nuclear receptor superfamily which is not normally present in the cells of said host, wherein expression of said receptor peptide is under the control of an inducible promoter, wherein said receptor peptide activates said regulatory element in the absence of an exogenous dimer partner therefor and in the presence of a ligand for said ligand binding domain; and (iii) said ligand for said ligand binding domain, wherein said ligand is not normally present in the cells of said host;

said method comprising subjecting said host to conditions suitable to induce expression of said receptor peptide.

In accordance with yet another embodiment of the present invention, there are provided methods for the expression of recombinant products detrimental to a host organism, said method comprising:

transforming suitable host cells with:

(i) a nucleic acid construct comprising a promoter and exogenous nucleic acid(s) which express said recombinant product under the control of a regulatory element; wherein said regulatory element is not normally present in the cells of said host, and (ii) nucleic acid encoding a receptor peptide comprising a DNA binding domain, and the ligand binding domain and hinge region of a non-mammalian member of the nuclear receptor superfamily which is not normally present in the cells of said host, wherein said receptor peptide activates said regulatory element in the absence of an exogenous dimer partner therefor and in the presence of a ligand for said ligand binding domain, and growing said host cells to the desired level in the substantial absence of ligand for said receptor peptide; and inducing expression of said recombinant product by introducing into said host cells a ligand, which, in combination with said receptor peptide, binds to said regulatory element and activates transcription therefrom.

Recombinant products detrimental to a host organism contemplated for expression in accordance with the present invention include any gene product that functions to confer a toxic effect on the organism. For example, inducible expression of a toxin such as the diptheroid toxin would allow for specific ablation of tissue (Ross et al. *Genes and Development* 7:1318–1324 (1993)). Moreover, the numerous gene products that are known to induce apoptosis in cells expressing such products are contemplated for use herein (see, e.g, *Apoptosis, The Molecular Basis of Cell Death*, Current Communications In Cell & Molecular Biology, Cold Spring Harbor Laboratory Press, 1991).

In accordance with still another embodiment of the present invention, there are provided methods for modulating the transcription of nucleic acid(s) in an in vitro system, said method comprising administering to said system an amount of said ligand effective to modulate the transcription of said nucleic acid(s); wherein said ligand is not normally present in said cellular system; wherein said system comprises:

(i) a nucleic acid construct comprising a promoter and said nucleic acid(s) under the control of a regulatory element; and (ii) nucleic acid encoding a receptor peptide comprising a DNA binding domain, and the ligand binding domain and hinge region of a non-mammalian member of the nuclear receptor superfamily which is not normally present in the cells of said host, wherein said receptor peptide activates said regulatory element in the absence of an exogenous dimer partner therefor and in the presence of a ligand for said ligand binding domain.

In accordance with yet another embodiment of the present invention, there are provided methods for the treatment of a host in need of gene therapy, said method comprising:

introducing into cells of said host:

(i) a nucleic acid construct comprising a promoter and said exogenous nucleic acid(s) under the control of a regulatory element;

(ii) nucleic acid encoding a receptor peptide comprising a DNA binding domain, and the ligand binding domain and hinge region of a non-mammalian member of the nuclear receptor superfamily which is not normally present in the cells of said host, wherein expression of said receptor peptide is under the control of an inducible promoter, wherein said receptor peptide activates said regulatory element in the absence of an exogenous dimer partner therefor and in the presence of a ligand for said ligand binding domain;

administering, to said host, ligand for said ligand binding domain.

As used herein, the term "in vivo delivery" refers to delivery of biological materials by such routes of administration as oral, intravenous, subcutaneous, intraperitoneal, intrathecal, intramuscular, intracranial, inhalational, topical, transdermal, suppository (rectal), pessary (vaginal), and the like.

In accordance with still another embodiment of the present invention, there are provided methods for the treatment of a host in need of gene therapy, said method comprising:

introducing into cells obtained from said host:

(i) a nucleic acid construct comprising a promoter and exogenous nucleic acid(s) under the control of a regulatory element; and (ii) nucleic acid encoding a receptor peptide comprising a DNA binding domain, and the ligand binding domain and hinge region of a non-mammalian member of the nuclear receptor superfamily which is not normally present in the cells of said host, wherein said receptor peptide activates said regulatory element in the absence of an exogenous dimer partner therefor and in the presence of a ligand for said ligand binding domain; and to provide modified cells;

reintroducing the modified cells into said host; and administering, to said host, ligand for said ligand binding domain.

In accordance with this embodiment of the present invention, the exogenous nucleic acid is introduced directly into cells obtained from a donor (host or separate donor). Such cells are then implanted within the host. In a presently preferred embodiment, the transplanted cells are autologous with respect to the host. Autologous means that the donor and recipient of the cells are one and the same.

Nucleic acid may be stably incorporated into cells or may be transiently expressed using methods known in the art. Cells are cultivated under growth conditions (as opposed to protein expression conditions) until a desired density is achieved. Stably transfected mammalian cells may be prepared by transfecting cells with an expression vector having a selectable marker gene (such as, for example, the gene for thymidine kinase, dihydrofolate reductase, neomycin resistance, and the like), and growing the transfected cells under conditions selective for cells expressing the marker gene. To prepare transient transfectants, mammalian cells are transfected with a reporter gene (such as the *E. coli* β-galactosidase gene) to monitor transfection efficiency. Selectable marker genes are typically not included in the transient transfections because the transfectants are typically not grown under selective conditions, and are usually analyzed within a few days after transfection.

The concept of gene replacement therapy for humans involves the introduction of functionally active "wild type" or "therapeutic" nucleic acids into the somatic cells of an affected host to correct a gene defect or deficiency. However, in order for gene replacement therapy to be effective, it must be possible to control the time and location at which gene expression occurs.

Genes that encode useful "gene therapy" proteins that are not normally transported outside the cell can be used in the invention if such genes are "functionally appended" to a signal sequence that can "transport" the encoded product across the cell membrane. A variety of such signal sequences are known and can be used by those skilled in the art without undue experimentation.

In yet another embodiment of the present invention, there are provided constructs comprising a promoter, a tetracycline-controlled transactivator, a VP16 activation domain, a DNA binding domain and *Bombyx mori*-derived ligand binding domain encoding sequence, wherein the components of the construct are operatively associated with the other components of the construct.

In yet another embodiment of the present invention, there are provided constructs comprising a VP16 activation domain operatively associated with a DNA binding domain and *Bombyx mori*-derived ligand binding domain encoding sequence.

In accordance with another embodiment of the present invention, there are provided gene transfer vectors useful for the introduction of invention constructs into suitable host cells. Such gene transfer vectors comprise a first reporter under the control of a regulatory element, a second reporter under the control of an operator which is responsive to a ligand-mediated receptor which confers responsiveness to antibiotics, and a construct comprising a promoter, a tetracycline-controlled transactivator, a VP16 activation domain, a DNA binding domain and *Bombyx mori*-derived ligand binding domain encoding sequence. The number of copies of regulatory elements can readily be varied by those of skill in the art. For example, transcription regulatory regions can contain from 1 up to about 50 copies of a particular regulatory element, preferably 2 up to about 25 copies, more preferably 3 up to about 10–15 copies, with about 4–6 copies being especially preferred Gene transfer vectors (also referred to as "expression vectors") contemplated for use herein are recombinant nucleic acid molecules that are used to transport nucleic acid into host cells for expression and/or replication thereof. Expression vectors may be either circular or linear, and are capable of incorporating a variety of nucleic acid constructs therein. Expression vectors typically come in the form of a plasmid that, upon introduction into an appropriate host cell, results in expression of the inserted nucleic acid.

Suitable expression vectors for use herein include a recombinant DNA or RNA construct(s), such as plasmids, phage, recombinant virus or other vectors that, upon introduction into an appropriate host cell, result(s) in expression of the inserted DNA. Appropriate expression vectors are well known to those of skill in the art and include those that are replicable in eukaryotic cells and/or prokaryotic cells and those that remain episomal or those which integrate into the host cell genome.

The amount of exogenous nucleic acid introduced into a host can be varied by those of skill in the art. For example, when a viral vector is employed to achieve gene transfer, the amount of nucleic acid introduced can be increased by increasing the amount of plaque forming units (PFU) of the viral vector.

As used herein, the phrase "transcription regulatory region" refers to that portion of a nucleic acid or gene construct that controls the initiation of mRNA transcription. Regulatory regions contemplated for use herein, in the absence of the non-mammalian transactivator, typically comprise at least a minimal promoter in combination with a regulatory element responsive to the ligand/receptor peptide complex. A minimal promoter, when combined with a regulatory element functions to initiate mRNA transcription in response to a ligand/receptor peptide complex. However, transcription will not occur unless the required inducer (ligand therefor) is present. To the contrary, when the non-mammalian transactivator, other than members of the nuclear receptor superfamily, is present in the host, the transactivator-responsive regulatory element will only induce transcription in the absence of ligand therefor.

As used herein, the phrase "operatively associated with" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and promoter such that the transcription of such DNA is initiated from the promoter by an RNA polymerase that specifically recognizes, binds to and transcribes the DNA.

Preferably, the transcription regulatory region further comprises a binding site for ubiquitous transcription factor (s). Such binding sites are preferably positioned between the promoter and the regulatory element. Suitable ubiquitous transcription factors for use herein are well-known in the art and include, for example, Sp1.

Expression vectors suitable for use in the practice of the present invention are well known to those of skill in the art and include those that are replicable in eukaryotic cells and/or prokaryotic cells as well as those that remain episomal and those that integrate into the host cell genome. Expression vectors typically further contain other functionally important nucleic acid sequences encoding antibiotic resistance proteins, and the like.

Exemplary eukaryotic expression vectors include eukaryotic constructs, such as the pSV-2 gpt system (Mulligan et al., (1979) Nature, 277:108–114); pBlueSkript (Stratagene, La Jolla, Calif.), the expression cloning vector described by Genetics Institute (Science, (1985) 228:810–815), and the like. Each of these plasmid vectors are capable of promoting expression of the receptor peptide of interest.

Suitable means for introducing (transducing) expression vectors containing invention nucleic acid constructs into host cells to produce transduced recombinant cells (i.e., cells containing recombinant heterologous nucleic acid) are well-known in the art (see, for review, Friedmann, (1989) Science, 244:1275–1281; Mulligan, (1993) Science, 260:926–932, each of which are incorporated herein by reference in their entirety). Exemplary methods of transduction include, e.g., infection employing viral vectors (see, e.g., U.S. Pat. Nos. 4,405,712 and 4,650,764), calcium phosphate transfection (U.S. Pat. Nos. 4,399,216 and 4,634,665), dextran sulfate transfection, electroporation, lipofection (see, e.g., U.S. Pat. Nos. 4,394,448 and 4,619,794), cytofection, particle bead bombardment, and the like. The transduced nucleic acid can optionally include sequences which allow for its extrachromosomal (i.e., episomal) maintenance, or the transduced nucleic acid can be donor nucleic acid that integrates into the genome of the host.

In a specific embodiment, a gene transfer vector contemplated for use herein is a viral vector, such as Adenovirus, adeno-associated virus, or herpes-simplex virus based vectors, and synthetic vectors for gene therapy, and the like (see, e.g., Suhr et al. (1993) Arch. of Neurol. 50:1252–1268). Preferably, a gene transfer vector employed herein is a retroviral vector. Retroviral vectors are gene transfer plasmids that have an expression construct containing an exogenous nucleic acid residing between two retroviral LTRs. Retroviral vectors typically contain appropriate packaging signals that enable the retroviral vector, or RNA transcribed using the retroviral vector as a template, to be packaged into a viral virion in an appropriate packaging cell line (see, e.g., U.S. Pat. No. 4,650,764).

Suitable retroviral vectors for use herein are described, for example, in U.S. Pat. Nos. 5,399,346 and 5,252,479; and in WIPO publications WO 92/07573, WO 90/06997, WO 89/05345, WO 92/05266 and WO 92/14829, each of which is hereby incorporated herein by reference, in their entirety. These documents provide a description of methods for efficiently introducing nucleic acids into human cells using such retroviral vectors. Other retroviral vectors include, for example, mouse mammary tumor virus vectors (e.g., Shackleford et al., (1988) PNAS, USA, 85:9655–9659), human immunodeficiency virus (e.g., Naldini et al. (1996) Science 272:165–320), and the like.

Various procedures are also well-known in the art for providing helper cells which produce retroviral vector particles which are essentially free of replicating virus. See, for example, U.S. Pat. No. 4,650,764; Miller, Human Gene Therapy, 1:5–14 (1990); Markowitz, et al., Journal of Virology, 61(4):1120–1124 (1988); Watanabe, et al., Molecular and Cellular Biology, 3(12):2241–2249 (1983); Danos, et al., PNAS, 85:6460–6464 (1988); and Bosselman, et al., Molecular and Cellular Biology, 7(5):1797–1806 (1987) which disclose procedures for producing viral vectors and helper cells which minimize the chances for producing a viral vector which includes a replicating virus.

Recombinant retroviruses suitable for carrying out the invention methods are produced employing well-known methods for producing retroviral virions. See, for example, U.S. Pat. No. 4,650,764; Miller, Human Gene Therapy, 1:5–14 (1990); Markowitz, et al., Journal of Virology, 61(4):1120–1124 (1988); Watanabe, et al., Molecular and Cellular Biology, 3(12):2241–2249 (1983); Danos, et al., PNAS, 85:6460–6464 (1988); and Bosselman, et al., Molecular and Cellular Biology, 7(5):1797–1806 (1987).

Thus, in one embodiment, a modular assembly retroviral vector (MARV) can be utilized to express receptor peptide and an antibiotic resistance gene (see FIG. 1C). A "covector" (referred to herein as MARSHA) is utilized to provide a nucleic acid construct comprising the promoter, the regulatory element and exogenous nucleic acid and a second antibiotic resistance gene. The MARSHA vector carrying exogenous nucleic acid also has LTRs modified to promote high-level expression only in the presence of the receptor peptide encoded by the MARV and exogenous ligand therefor. Co-infected primary mammalian cells can then be selected using both antibiotics, resulting in a cell population that is dependent on ligand for high-level expression of the exogenous nucleic acid.

By introducing all of the necessary regulatory machinery, plus exogenous nucleic acid, selectable markers, and nucleic acid encoding receptor peptide, on the MARV retroviruses, highly efficient insertion of exogenous nucleic acids into targeted cells can be achieved.

Thus, the above-described viral constructs address several important problems confronted in the use of retroviruses in application of therapeutic gene transfer strategies to a variety of human diseases. For example, the retroviral vectors of the invention are capable of prolonged gene expression under conditions where conventionally integrated retroviruses are no longer transcriptionally active.

The invention will now be described in greater detail by reference to the following non-limiting examples.

EXAMPLE 1

Construction of Lepidopteran-derived Fusion Receptor Peptide

Figure 1A:
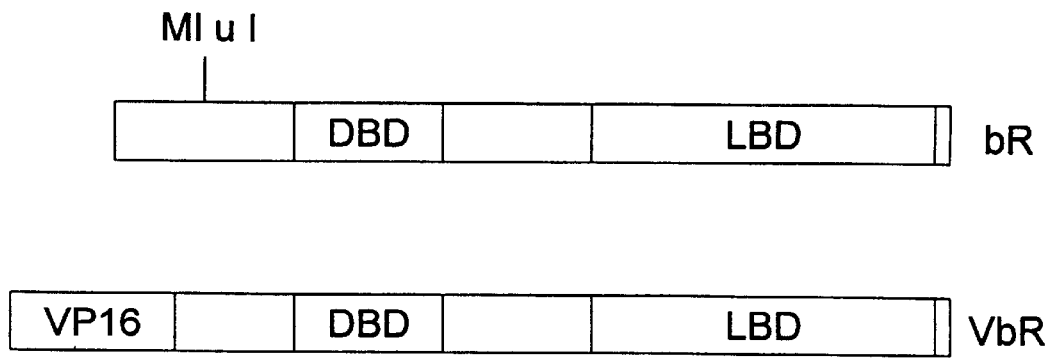
FIG. 1A provides a schematic drawing of the nuclear receptor protein isolated from the silk moth *Bombyx mori* (bR), as well as a construct containing a VP16 activation domain fused at an internal MluI site near the N-terminus of the *Bombyx mori* nuclear receptor, referred to as VbR.
Figure 1B:
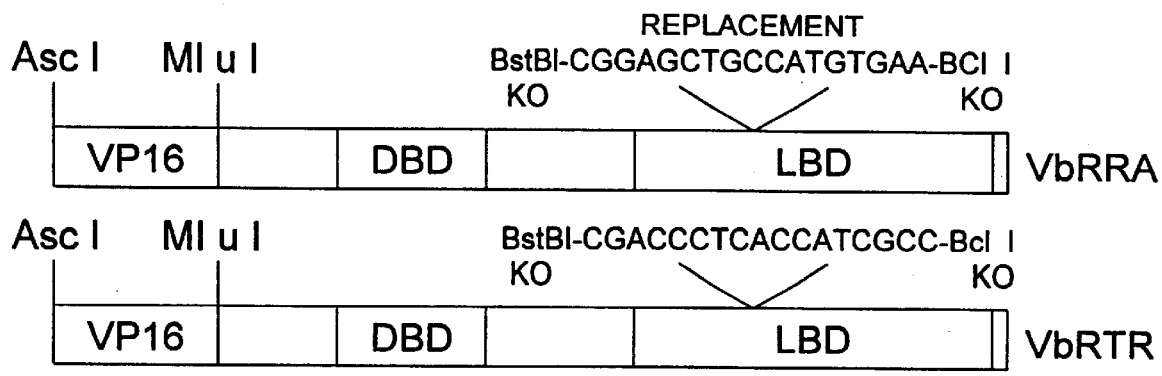
FIG. 1B depicts the replacement of several amino acids of the ligand binding domain of the *Bombyx mori* nuclear receptor with sequences from the retinoic acid receptor or the thyroid hormone receptor (VbRRA and VbRTR, respectively).
Figure 1C:
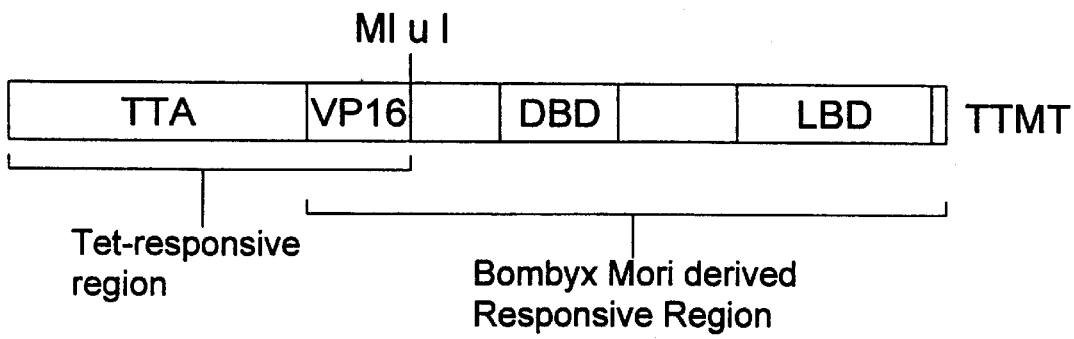
FIG. 1C provides a schematic of a hybrid transactivating construct, designated TTMT, containing a tetracycline-responsive transactivator (Tet-responsive region), a VP16 activation domain and a peptide derived from *Bombyx mori*.

The VP16 t-domain (activation domain) is fused in frame onto Bombyx mori-derived nuclear receptor (bR) at an internal MluI site near the N-terminus (VbR, FIG. 1A). An AscI site immediately downstream of the ATG start codon allows multimerization of VP16 domains for VbRs with multiple VP16 activation domains. Note that unlike Drosophila ecdysone receptor (dEcR), bR has virtually no C-terminal domain downstream of the LBD. Several amino acids of the hormone binding domain are replaced with sequences from the retinoic acid receptor or the thyroid hormone receptor (VbRRA and VbRTR, respectively) (FIG. 1B). These mutant variations have properties slightly different from VbR, and in addition have silent mutations that eliminate BclI and BstBI sites in VbR. These have been helpful in the construction of many VbR-based retroviral constructs.

EXAMPLE 2

Construction of Multifunctional Regulatory Proteins

The small size and simplicity of the VbR system lends itself to the development of multifunctional regulatory proteins which is functional on both hormone receptor and TTA responsive promoters. VbR fusions to the tetracycline transactivator results in a hybrid protein called TTMT (for Tebufenozide/Tetracycline Modulated Transactivator; see FIG. 1C). This protein functions jointly as a ligand-modulated regulator of gene expression from both tetO and EcRE (ecdysone response element)-containing promoters either separately or simultaneously. This compact protein, encoded in approximately 3 kb, confers constitutive activation of promoters containing tetracycline operators (tetOs) in the absence of tetracycline/analogs. In the presence of tet analogs, the TetO-binding function of TTMT is blocked, deactivating responsive promoters. The VbR half of the chimeric protein is constitutively inactive on EcRE-containing promoters, but may be stimulated to transactivate responsive promoters to a high level by the addition of murA or tebufenozide (teb). Through such a dual system, two separate responsive promoters may be regulated by two separate ligands simultaneously by a single protein. Additional variants using the reverse-Tet-transactivator, other VbR variants, novel response elements, and other regulatory proteins, will presumably result in further customized variations on this same theme.

A single transgenic animal generated with the TTMT protein would be responsive to transgene regulation of two separate transgenes by two separate ligands simultaneously. Further, individual promoters can be produced that respond to both halves of the protein, allowing the transgene to be regulated by both ligands, at the discretion of the investigator.

EXAMPLE 3

Transient Transfection Assay

Transient transfection experiments are carried out in CV-1 cells or 293 cells using modified drosophila ecdysone receptor (VdEcR) or modified bombyx hormone receptor (VbR) with or without dimer partners, as previously described. Luc activity is examined 40 hours after transfection and stimulation with ligand (FIG. 2A). Both receptors are assayed in CV-1 cells with 1 $\mu$M MurA and no exogenous dimer partner. Note that bR responds, while dEcR does not. Both receptors are also assayed in the presence of 5 $\mu$g/ml tebufenozide (FIG. 2B). Note that VbR responds with greater than 200-fold induction while drosophila EcR does not respond at all, and in fact, decreases slightly. Both receptors are also assayed with and without dimer partners. VbR is stimulated with 5 $\mu$g/ml tebufenozide and VdEcR is stimulated with 1 $\mu$M MurA. Note that RXR and Usp are necessary for VdEcR while VbR is constitutively activated by the presence of exogenous dimer partner and is inhibited by ligand addition. VbR, with no exogenous dimer partner, has an extremely low base-line which is stimulated 200–300 fold by ligand. Note also from this experiment that VdEcR tends to have a much higher baseline than VbR without dimer partner.

A side-by side comparison of 2.5 $\mu$g/ml teb and 1 $\mu$M MurA on VbR show both ligands are effective at stimulating VbR. Tebufenozide is administered to cells co-transfected with nucleic acids encoding receptors: LINX (which encodes the tet-transactivator (TTA)), VbR, TTMT (which encodes the TTA-VbR fusion protein, and TTMT-2V which is like TTMT, but with two VP16 t-domains) to assay for EcRE-Luc activity (FIG. 2C). Note that teb stimulates VbR, and the TTMT fusions, but has no action on TTA (LINX). The same experiment as that described for 2C, only with a TetO-Luc reporter, which responds only to TTA or fusion proteins is summarized in FIG. 2D. Doxycycline acts to block constitutive activity of TTA. Note that in this experiment, TTMT and TTMT-2V work better than TTA only (LINX) to stimulate the TetO-luc promoter/reporter. They are also efficiently blocked by dox. An experiment on CV-1 cells transfected with TTMT and two reporters: 6TetO-luc and 4-EcRE-bgalactosidase show both promoters could be simultaneously influenced by the presence or absence of both ligands (FIG. 2E).

EXAMPLE 4

Ligand Mediated Transgene Regulation

Transgene regulation by teb or MurA in stably infected rat fibroblasts is assayed utilizing MARSHA constructs as the reporter, and VbR encoding retroviral vectors to provide the receptor. Bulk infected selected populations stimulated with 2.5 $\mu$g/ml teb or 1 $\mu$M MurA indicate b-gal or tyrosine hydroxylase infected cells. Quantitative analysis of an individual VbR-luc clonal fibroblast line, and a VbR-GH clonal line show that 0.25 $\mu$g/ml teb is as effective at stimulating full activity as higher levels (FIG. 3).

EXAMPLE 5

Single-plasmid Retroviral Constructs pBO utilizes a responsive internal promoter "E" to regulate transgene expression and also contains a VbR-responsive 3' LTR to autoregulate the VbR receptor itself (FIG. 4). pNA is built along the lines of MARSHA, and uses a 3'-responsive LTR to regulate transgene expression. pBO utilizes an EcR responsive internal promoter and a TTA responsive 3' LTR. Both are host to regulation by the TTMT protein, simultaneously. The purpose of this design is to provide chronic stimulation of the duplicated 5' LTR along with regulated expression of the internal EcR responsive promoter. By removing all of the native promoting sequences from the 6 To LTR with the exception of the TetO's, variants of this construct are also inactivateable.

EXAMPLE 6

Construction of Plasmid Vectors

VbR and TTMT systems including constitutive and responsive promoters are integrated into a modular plasmid vector known as "pBW" (FIG. 5). The purpose of pBW is to integrate all of the elements of bombyx receptor- or tetracycline-analog responsiveness into a single plasmid vector destined for use in producing transgenic animals by methods such as pronuclear injection. pBW is to facilitate construction of transgenic animals or stably transfected cells using VbR variants. The pBW design simplifies the insertion of responsive promoters, transgenes, constitutive promoters, and the various VbRs, TTMTs, and related regulatory proteins. With pBW, the transgene regulatory properties of generated animals should more predictable and reproducible from founder to founder than multi-vector systems.

There are two major components of this system: the first is a tissue-specific expression cassette to produce the receptor and/or antibiotic resistance genes. The second is an expression cassette with a responsive promoter and a transgene. Polyadenylation signals flank all of the expression cassettes to provide efficient p(A) of transcribed RNAs. The use of rare restriction endonuclease sites within strategic locations and polylinkers of pBW will ease cloning of transgenes. An adjunct shuttle vector derived from pBSK (Stratagene) called SKSP contains rare sites flanking the polylinker and compatible with pBW. pBW also shares a number of sites with pBO to further simplify construction. pBW is constructed within the plasmid pcDNA3 (Invitrogen).

EXAMPLE 7

Regulating Transgene Expression in Target Cells in vitro

MARV is constructed in a modular fashion with individual elements of the recombinant retrovirus inserted sequentially. MARV starts as a polylinker composed of 5' NotI-MluI-NruI-EcoRI-AscI-PmlI-BstBI-BamHI-HindIII-HpaI-ClaI-NsiI-KpnI 3' sites. The retroviral Ψgln (see Adam and Miller in *J. Virol.* 62:3802 (1988) and Barklis et al., in *Cell* 47:391 (1986)) is inserted SmaI-EcoRI into the NruI-EcoRI sites of the MARV polylinker. The internal CMV promoter is inserted BamHI-ClaI into the BamHI-ClaI sites of the evolving MARV vector. All LTRs destined for insertion into the 5' location are produced by low-cycle/high-fidelity PCR production and end primers with compatible NotI-MluI sites for insertion into the NotI-MluI sites of MARV. 3' LTRs are generated with ClaI-NsiI compatible ends for insertion into these sites. The R region of the 3' LTR is included in the downstream primer sequence. Transgenes, receptor cDNAs, or selectable marker genes are inserted into the remaining polylinker from the EcoRI site through the BamHI site, or the remaining polylinker after the internal promoters (HindIII-ClaI). By proceeding in this fashion, and taking advantage of the modular design to swap in new modifications, a variety of MARV and MARSHA vectors are constructed.

The resulting vectors are characterized by restriction digests and mapping, amplified by large-scale plasmid preparation, and prepared for transfection into packaging cells by standard methods. Transient retroviral production in 293 and 293T cells has been previously described (see Pear et al., in *PNAS* 90:8392 (1993)). Forty-eight hours after transient retroviral production, the conditioned media is removed, filtered through 0.45 mm filters, and frozen at −70° C. until use. 10-cm dishes of primary-cultured Fisher rat abdominal fibroblasts (Rosenberg et al., *Science* 242:1575 (1988)) at approximately 50% density are infected with 1/10 volume of virus-containing media and 8 μg polybrene/ml for 48 hours. Infected cells are then selected under the appropriate antibiotic until non-infected cells are cleared from the population (approximately 10 days). Resistant colonies are trypsinized, pooled and passaged. The resulting population is then infected with the second virus, and reselected again in media containing both antibiotics. The infection and selection process for the second round of viral infection proceeds as described for the first round. The final population of doubly resistant primary fibroblasts are then pooled and passaged to 6 or 24-well Costar plates for assay in vitro.

The short (24 hour) course is performed in 24-well Costar dishes with cells at approximately 80% confluency. 5 μl of ligand (final concentration of 1 μM) or vehicle (20% EtOH) is added to the 1 ml of media in each well. Eight hours after first ligand administration, the cells are all washed in PBS and the media is replaced. β-galactosidase histochemical reaction is performed on 1.5% glutaraldehyde-fixed cells essentially as described by Shimohama et al. in *Brain Res Mol Brain Res* 5:271 (1989) in a 37° C. environment for 2 hours. The 4-day time course is performed in an identical fashion, except that the cell population is plated at only 20% confluency at the start of the experiments (and grow to near-total confluency by the end of the 4 day period) and neither ligand nor media is changed or replaced.

For long-term culture experiments, MMBG fibroblasts are plated in triplicate at high density in 24-well plates. Within 48–72 hours of plating, when the cells reach 100% confluency within the wells, 1 μM ligand or vehicle is added to one group of plates, while others are left completely untreated. The wells are then placed in a 37° C.-10% $CO_2$ environment for the next 25 days without any media changes. On day 23, the plates that had received neither vehicle nor ligand on day 1 are removed and half of the wells are given vehicle and the other half are given 1 μM ligand for 40 hours.

After 25 days of nutrient deprivation and contact inhibition, all of the plates are processed for βgal histochemical staining as above.

MMGH fibroblasts are produced by infection of a MARV-infected fibroblast line with the MARSHA-GH virus. Cells are selected under both antibiotics as described previously. After preliminary examination of ligand-induced hGH production in the bulk population, the MMGH population is plated at high density in 6-well Costar plates. Forty-eight hours after the initial plating and when the cells are essentially completely growth inhibited by contact, the medium of all plates is replaced with DME containing 2% FBS. Under these conditions, primary rat fibroblasts stop dividing even if they are not confluent, and settle out into a distended morphology with prominent nuclei characteristic of severely growth-arrested fibroblasts. Six days after acclimatization to this culture environment, 1 ml of medium is harvested from each well and plate of the experiment and stored frozen at −20° C. The remaining unused media is discarded at the same time of harvest and replaced with fresh DME-2% FBS. Groups of wells are treated or not with 1 μM ligand. Hormonally treated wells are washed with medium to remove as much residual ligand as possible prior to medium replacement when ligand treatment is discontinued. This routine is repeated daily for the 21-day extent of the experiment.

After all time-point samples have been collected and frozen at −20° C., they are simultaneously processed for the presence of the hGH protein by ELISA (Boehringer Mannheim) following the protocol recommended by the manufacturer. ELISA data are quantitated on an MR700 microplate reader (Dynatech Laboratories, Chantilly, VA) and compared to a standard curve generated using purified hGH to determine picogram GH amounts. Control wells are MARV/MARSHA-TH (tyrosine hydroxylase) producing fibroblasts, but display all of the MARV/MARSHA characteristics except for the hGH transgene and secreted protein.

EXAMPLE 8

Transient Transfections

Transient transfections are performed by calcium-phosphate coprecipitation employing standard methods (see Sambrook et al., in Molecular Cloning: A Laboratory Manual.

Cold Spring Harbor Press, New York, N.Y. (1989)). All tissue culture experiments are performed using DMEM 10% FBS in a 10% $CO_2$ incubator unless otherwise specified. All transfections are performed in triplicate in 24-well Costar plates using CV-1 cells at an approximately $5\times10^4$ plating density. Immediately following transfection, 1 μm ligand in 20% EtOH/PBS is added to wells. After 40 additional hours of incubation, cells are harvested and luciferase activity measured in an analytical bioluminescence photometer. Cell extracts are simultaneously examined for LacZ activity of the internal control by standard methods Bar graph levels represent relative luciferase activity after correction using internal control values. All molecular biology enzymes and reagents used in this study are provided by either NEB (Beverly, Mass.) or Strategene (La Jolla, Calif.).

EXAMPLE 9

Prolonged Transgene Expression for either/or ex vivo Gene Therapy Applications

Autologous, explanted skin fibroblasts genetically modified to express tyrosine hydroxylase (TH), the enzyme responsible for synthesis of L-dopa and the precursor for the neurotransmitter dopamine, have proven to ameliorate a loss of local dopamine in animal models of Parkinson's disease. Although quite effective in providing dopamine to the area of neural damage, this technique is only therapeutically useful for 2–3 weeks following transplantation. The decrease in effectiveness has been traced back to a dramatic loss of TH transgene expression in transplanted, post-mitotic cells. The use of invention constructs allows one to overcome the loss of transgene expression by providing stimulation of the retroviral LTR promoter through either ligand-activated transactivating complexes or through constitutive transactivating receptor variants. In this way, transgene expression may be maintained for longer periods of time, even indefinitely if desired.

Stem-type cells, such as stem cells of the hematopoetic system, nervous system, or embryo, could be infected or transfected with VbR regulated transgenes and subsequently implanted into adult, fetus, or early embryonic animals for either therapeutic or research purposes. Cells of the hematopoetic system could conditionally express proteins producing blood clotting factors such as factor IX, metabolic factors such as glucocerebrosidase, or protective factors including anti-HIV proteins.

EXAMPLE 10

Prolonged Transgene Expression for Either in vivo Gene Therapy Applications

The small size and regulatory capacity of VbRs lend themselves to use in recombinant retroviruses as a method of gene transfer. VbRs have been introduced into both MLV and lentiviral-based retroviral systems. When these viruses are introduced directly into target cells of either a mature or developing organism, expression of the virally encoded transgenes may be regulated by systemic addition of ligands such as tebufenozide and derivatives. An example of a disease that could be theoretically ameliorated by application of in vivo VbR encoding retroviruses is Parkinson's disease, described above.

Another application would be to use VbR encoding retroviruses as an anti-viral agent. Lentiviral vectors with regulated properties and harboring suicide genes or "protective" proteins could be used as a means of conditionally depleting or destroying HIV-positive cells.

EXAMPLE 11

Modulated Transgene Expression for Either in vivo or ex vivo Gene Therapy Application Treatment of Parkinson's disease with the chemical precursor of dopamine, L-dopa, has proven effective in ameliorating many of the deficits of Parkinsonism. With time, however, patients become refractory to L-dopa therapy, with the deleterious effects of chronic treatment outweighing even the serious symptoms of the disease itself. Eventually, patients are left with few therapeutic options. While the transplantation of TH expressing cells may be effective when constantly producing low-levels of L-dopa, a potentially far more beneficial approach would be to allow the physician some degree of control over L-dopa production in the patient. This would allow sufficient control to ensure that the transgenic factor is expressed at appropriate therapeutic levels. At times when endogenous systems are capable of providing full function, the transgene may be allowed to become quiescent and transcriptionally inactive until needed again. Because the transcriptional induction of the invention retroviral constructs is dependent on an exogenous ligand, expression of an integrated therapeutic transgene can be placed under the control of the physician and patient.

EXAMPLE 12

Use of Invention for Efficient Production of Transgenic Animals

Transgenic animals are generally produced by either pronuclear injection of DNA or by transfection of embryonic stem (ES) cells followed by selection and injection of the stem cell into the inner cell mass of very early embryos. Pronuclear injection results in approximately 5–10% stable gene transfer in the production of transgenic mice. The use of ES cells in producing transgenics is likewise inefficient in generating mosaics with germ-line transmission of the transgene. It was proposed in the mid-1980's to use retroviruses to transfer transgenes with high efficiency into early embryos or ES cells to dramatically enhance the odds of producing transgenic animals. All attempts at this failed, not because the virus was incapable of stably integrating into the target cell genome, but because the integrated provirus did not express any of the genes encoded within the viral transcriptional cassette.

The present invention is capable of overcoming the transcriptional block to result in germ-line transgenic animals with full expression from the integrated transgene. In addition to expressing the transgene, the level of transcription may still be regulated by controlling the supply of ligand to the transgenic animal The increased efficiency of producing transgenic animals by retroviral infection should open up the way to producing mutant animals of a variety of species previously impractical for genetic modification because of the potential cost of producing a large number of non-positive animals by classical methods.

To produce transgenic mice, the following nucleic acid constructs are prepared and subsequently injected into fertilized eggs: CD3-VbR and a ligand inducible S-gal reporter. Two separate lines of transgenic mice are generated harboring either a ligand inducible reporter; or a T-cell specific expression construct of VbR, respectively. The former are referred to as reporter mice, the latter are referred to as receptor mice, and double transgenic mice are referred to as receptor/reporter mice. Constructs CD3-VbR are injected, while the reporter is injected alone. Primary genotyping is performed by Southern blot analysis and the transmission of transgenic mice is monitored by dot blot analysis. Receptor mice are analyzed for VbR expression by Northern blot analysis of RNA collected from these mice. For Northern blot analysis, 15 µg of total RNA obtained from the thymus, and various tissues as a control, is run on a denaturing gel and blotted onto a nitrocellulose membrane. The blot is probed with a radiolabeled β-gal-specific probe and exposed on film for 2 days. In addition; the transgene can be transferred to the offspring as expected by Mendelian genetics.

EXAMPLE 13

Use of Retroviral Constructs in the Invention for Efficient Gene Transfer to Developing Embryos Since the present invention can effectively overcome the block of viral expression in embryonic cells, invention constructs are a potent tool in the delivery of transgenes to somatic tissues of a developing embryo. With many diseases, considerable damage is done during embryonic development so that therapies applied after birth are essentially ineffective to ameliorate the disease phenotype.

The present invention can infect cells of the embryo and can provide therapeutic factors to the developing fetus either constitutively, or under the regulation of exogenously produced ligand.

EXAMPLE 14

Use of Vector Constructs in Invention with Inducible High Titers

One obstacle in the use of retroviruses as gene transfer agents is that titers of retroviruses from existing producer cell lines are only on the order of $1 \times 10^4$ or $1 \times 10^5$. By using a retroviral construct of the invention having intact enhancers and regulatory elements, expression of the retrovirus may be induced by greater than ten-fold, resulting in correspondingly higher titers of infectious virus.

While the invention has been described in detail with reference to certain preferred embodiments thereof, it will be understood that modifications and variations are within the spirit and scope of that which is described and claimed.

That which is claimed is:

1. A nucleic acid construct for regulation of transgene expression in a mammalian host cell, said construct encoding a chimeric nuclear receptor peptide comprising:
a hinge region of a lepidopteran receptor bounded by a ligand binding domain not normally present in the host cell and a DNA binding domain such that the receptor peptide, upon binding exogenous ligand, binds to a regulatory element and activates transcription,
wherein said hinge region has more than 80% sequence identity with amino acid residues 273–299 of SEQ ID NO:3 and promotes association of the chimeric nuclear receptor peptide with an endogenous nuclear receptor.

2. A nucleic acid construct according to claim 1 wherein said chimeric nuclear receptor peptide further comprises an activation domain.

3. A nucleic acid construct according to claim 1 wherein said ligand binding domain has more than 80% sequence identity with amino acid residues 363–586 of SEQ ID NO:3, and wherein said ligand binding domain binds exogenous ligand for said chimeric nuclear receptor peptide.

4. A nucleic acid construct according to claim 1 wherein the nucleic acid encoding said ligand binding domain encodes amino acid residues 363–586 of SEQ ID NO:3, or a nucleotide sequence fully complementary over the entire length of said domain.

5. A nucleic acid construct according to claim 1 wherein said DNA binding domain is obtained from a DNA-binding protein.

6. A nucleic acid construct according to claim 5 wherein said DNA binding domain is obtained from a member of the nuclear receptor superfamily.

7. A nucleic acid construct according to claim 6 wherein said DNA binding domain is obtained from a lepidopteran receptor.

8. A nucleic acid construct according to claim 6 wherein said DNA binding domain is obtained from a Drosophila receptor.

9. A nucleic acid construct according to claim 1 wherein said nucleic acid construct further comprises a regulatory element operatively associated with at least one exogenous nucleic acid, and wherein the receptor peptide, upon binding exogenous ligand, binds to said regulatory element and activates transcription of said exogenous nucleic acid.

10. A nucleic acid construct according to claim 7 wherein said regulatory element comprises at least one hormone response element.

11. A nucleic acid construct according to claim 7 wherein said at least one exogenous nucleic acid is selected from wild type and therapeutic nucleic acids.

12. A nucleic acid construct according to claim 1 wherein said construct further comprises a selectable marker gene.

13. A nucleic acid construct according to claim 1 wherein the hinge region has more than 80% sequence identity with amino acid residues 273–362 of SEQ ID NO:3.

14. A nucleic acid construct according to claim 1 wherein nucleic acid encoding the ligand binding domain comprises at least 46 or more contiguous nucleotides encoding any contiguous segment of amino acid residues 363–586 of SEQ ID NO:3, wherein said ligand binding domain binds exogenous ligand for said chimeric nuclear receptor peptide, and wherein nucleic acid encoding the hinge region comprises nucleic acid that encodes at least the 27 contiguous amino acid residues of amino acid residues 273–299 of SEQ ID NO:3, or a nucleotide sequence fully complementary over the entire length of said ligand binding domain and said hinge region.

15. An expression cassette comprising a promoter operatively associated with a nucleic acid construct according to claim 1.

16. A viral vector capable of ligand-mediated expression, wherein said vector comprises an expression cassette according to claim 15.

17. A viral vector according to claim 16 wherein said viral vector further comprises a retroviral psi (Ψ) packaging signal and a 5' and/or a 3' long terminal repeat (LTR).

18. An animal cell in culture which is transformed with a nucleic acid construct according to claim 1.

19. An expression system comprising:
a first nucleic acid construct for regulation of transgene expression in a mammalian host cell, said construct encoding a chimeric nuclear receptor peptide comprising:
a hinge region of a lepidopteran receptor bounded by a ligand binding domain not normally present in the host cell and a DNA binding domain such that the receptor peptide, upon binding exogenous ligand, binds to a regulatory element and activates transcription,
wherein said hinge region has more than 80% sequence identity with amino acid residues 273–299 of SEQ ID NO:3 and promotes association of the chimeric nuclear receptor peptide with an endogenous nuclear receptor, and
a second nucleic acid construct comprising at least one regulatory element operatively associated with at least one exogenous nucleic acid, wherein the receptor peptide, upon binding exogenous ligand, binds to said regulatory element and activates transcription of said exogenous nucleic acid.

20. An expression system according to claim 19 wherein the nucleic acid encoding the ligand binding domain comprises at least 46 or more contiguous nucleotides encoding any contiguous segment of amino acid residues 363–586 of SEQ ID NO:3, wherein said ligand binding domain binds exogenous ligand for said chimeric nuclear receptor peptide, and wherein the nucleic acid encoding the hinge region encodes at least 27 contiguous amino acid residues of amino acid residues 273–299 of SEQ ID NO:3.

21. An expression system according to claim 19 wherein the hinge region has more than 80% sequence identity with amino acid residues 273–362 of SEQ ID NO:3.

22. An expression system according to claim 19 wherein the ligand binding domain of said first nucleic acid construct has more than 80% sequence identity with amino acid residues 363–586 of SEQ ID NO:3, and wherein said ligand binding domain binds exogenous ligand for said chimeric nuclear receptor peptide.

23. A nucleic acid construct comprising nucleic acid encoding a VP16 activation domain, a DNA binding domain, a ligand binding domain, and a hinge region of a lepidopteran receptor, wherein said hinge region promotes association of the receptor peptide encoded by said construct with an endogenous dimer partner and has more than 80% sequence identity with amino acid residues 273–299 of SEQ ID NO:3.

24. A nucleic acid construct according to claim 23 wherein the nucleic acid encoding the ligand binding domain comprises at least 46 contiguous nucleotides encoding any contiguous segment of amino acid residues 363–586 of SEQ ID NO:3, wherein said ligand binding domain binds exogenous ligand for said chimeric nuclear receptor peptide, and wherein nucleic acid encoding the hinge region encodes amino acid residues 273–299 of SEQ ID NO:3, and nucleotide sequences fully complementary over the entire length of said ligand binding domain and said hinge region.

25. A nucleic acid construct according to claim 23 wherein the hinge region has more than 80% sequence identity with amino acid residues 273–362 of SEQ ID NO:3.

26. A nucleic acid construct according to claim 23 wherein said ligand binding domain has more than 80% sequence identity with amino acid residues 363–586 of SEQ ID NO:3, wherein said ligand binding domain binds exogenous ligand for said chimeric nuclear receptor peptide.

27. A nucleic acid construct comprising, in operative association with one another, a promoter and nucleic acid encoding a tetracycline-controlled transactivator, a VP16 activation domain, a DNA binding domain, a ligand binding domain, and a hinge region of a lepidopteran receptor, wherein said hinge region promotes association of the receptor peptide encoded by said construct with an endogenous dimer partner and has more than 80% sequence identity with amino acid residues 273–299 of SEQ ID NO:3.

28. A nucleic acid construct according to claim 27 wherein nucleic acid encoding the ligand binding domain comprises at least 46 contiguous nucleotides encoding any contiguous segment of amino acid residues 363–586 of SEQ ID NO:3, and wherein said ligand binding domain binds exogenous ligand for said chimeric nuclear receptor peptide, and nucleotide sequences fully complementary over the entire length of said domain.

29. A nucleic acid construct according to claim 27 wherein said ligand binding domain has more than 80% sequence identity with amino acid residues 373–596 of SEQ ID NO:3, wherein said ligand binding domain binds exogenous ligand for said chimeric nuclear receptor peptide.

30. A nucleic acid construct according to claim 27 wherein the hinge region has more than 80% sequence identity with amino acid residues 273–362 of SEQ ID NO:3.

31. A vector comprising:
   a first reporter gene under the control of a regulatory element,
   a second reporter gene under the control of an operator which is responsive to a ligand-mediated receptor which confers responsiveness to tetracycline and analogs thereof, and
   a nucleic acid construct comprising a promoter operatively associated with nucleic acid encoding a tetracycline-controlled transactivator, a VP16 activation domain, a DNA binding domain, a ligand binding domain, and a hinge region, wherein said hinge region has more than 80% sequence identity with amino acid residues 273–299 of SEQ ID NO:3 and promotes association of the receptor peptide encoded by said construct with an endogenous nuclear receptor.

32. A vector according to claim 31 wherein nucleic acid encoding the ligand binding domain comprises at least 46 contiguous nucleotides encoding any contiguous segment of amino acid residues 363–586 of SEQ ID NO:3, and wherein said ligand binding domain binds exogenous ligand for said chimeric nuclear receptor peptide, and nucleotide sequences fully complementary over the entire length of said domain.

33. A vector according to claim 31 wherein said ligand binding domain has more than 80% sequence identity with amino acid residues 363–586 of SEQ ID NO:3, wherein said ligand binding domain binds exogenous ligand for said chimeric nuclear receptor peptide.

34. A vector according to claim 31 wherein the hinge region has more than 80% sequence identity with amino acid residues 273–362 of SEQ ID NO:3.

35. A nucleic acid construct for regulation of transgene expression in a mammalian host cell, said construct encoding a nuclear receptor peptide comprising:
   a hinge region of a lepidopteran receptor bounded by a ligand binding domain not normally present in the host cell and a DNA binding domain such that the receptor peptide, upon binding exogenous ligand, binds to a regulatory element and activates transcription,
   wherein said hinge region has more than 80% sequence identity with amino acid residues 273–299 of SEQ ID NO:3 and promotes association of the nuclear receptor peptide with an endogenous nuclear receptor, and
   wherein at least one of said ligand binding domain and said DNA binding domain are not derived from said lepidopteran receptor.

36. A nucleic acid construct according to claim 35 wherein said ligand binding domain is not derived from said lepidopteran receptor.

37. A nucleic acid construct according to claim 35 wherein said DNA binding domain is not derived from said lepidopteran receptor.

38. A nucleic acid construct according to claim 35 wherein said nuclear receptor peptide further comprises an activation domain.

39. A nucleic acid construct according to claim 38 wherein said activation domain is not derived from said lepidopteran receptor.

* * * * *

UNITED STATES PATENT AND TRADEMARK OFFICE
CERTIFICATE OF CORRECTION

PATENT NO. : 6,300,488 B1  
DATED : October 9, 2001  
INVENTOR(S) : Gage et al.

It is certified that error appears in the above-identified patent and that said Letters Patent is hereby corrected as shown below:

<u>Column 37,</u>  
Lines 45 and 48, after the word claim, delete "7" and insert -- 9 --

Signed and Sealed this

Fourteenth Day of May, 2002

*Attest:*

JAMES E. ROGAN  
*Attesting Officer*  *Director of the United States Patent and Trademark Office*

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
        (A) LENGTH: 71 amino acids
        (B) TYPE: amino acid
        (C) STRANDEDNESS: single
        (D) TOPOLOGY: linear (xi) SEQUENCE DESCRIPTION: SEQ ID NO:1:

```
Cys Xaa Xaa Cys Xaa Xaa Asp Xaa Ala Xaa Gly Xaa Tyr Xaa Xaa Xaa
 1               5                  10                  15

Xaa Cys Xaa Xaa Cys Lys Xaa Phe Phe Xaa Arg Xaa Xaa Xaa Xaa Xaa
            20                  25                  30

Xaa Xaa Xaa Xaa Xaa Xaa Cys Xaa Xaa Xaa Xaa Xaa Xaa Xaa Xaa Cys
        35                  40                  45

Xaa Xaa Xaa Lys Xaa Xaa Arg Xaa Xaa Cys Xaa Xaa Cys Arg Xaa Xaa
    50                  55                  60

Lys Cys Xaa Xaa Xaa Gly Met
65                  70
```

(2) INFORMATION FOR SEQ ID NO:2:

(i) SEQUENCE CHARACTERISTICS:
        (A) LENGTH: 2711 base pairs
        (B) TYPE: nucleic acid
        (C) STRANDEDNESS: single
        (D) TOPOLOGY: linear (ix) FEATURE:
        (A) NAME/KEY: Coding Sequence
        (B) LOCATION: 185...2002
        (D) OTHER INFORMATION:

(xi) SEQUENCE DESCRIPTION: SEQ ID NO:2:

```
CTCCGTTGAC GACGGTCGCG CGTGCGGTAC GTCCGTTTTT ACGGCTCAAA CGTACACGGT      60

AACCTCCGTC TCTGCATCAT CGGCGGAACT CGTGAAATTC GCGTGCTTTT CTCACCTGTT     120

GAACGAGTTG TGTTGTGACT GAAAAACATC ATCACAAATA TCAAGCTTCA AAACTAATAA     180

GTGA ATG AGA GTC GAG AAC GTG GAT AAC GTA TCG TTT GCT TTG AAC GGA     229
     Met Arg Val Glu Asn Val Asp Asn Val Ser Phe Ala Leu Asn Gly
      1               5                  10                  15

CGC GCT GAC GAG TGG TGT ATG TCT GTA GAG ACG CGT TTA GAT AGT TTA     277
Arg Ala Asp Glu Trp Cys Met Ser Val Glu Thr Arg Leu Asp Ser Leu
```

-continued

```
                       20                  25                  30
GTG CGA GAA AAA AGT GAA GTG AAA GCC TAC GTC GGA GGA TGT CCC TCG                325
Val Arg Glu Lys Ser Glu Val Lys Ala Tyr Val Gly Gly Cys Pro Ser
                35                  40                  45

GTA ATC ACG GAT GCT GGA GCG TAT GAC GCG CTC TTC GAC ATG AGA CGC                373
Val Ile Thr Asp Ala Gly Ala Tyr Asp Ala Leu Phe Asp Met Arg Arg
         50                  55                  60

CGC TGG TCT AAT AAC GGT GGC TTC CCG CTG CGA ATG CTT GAA GAG AGC                421
Arg Trp Ser Asn Asn Gly Gly Phe Pro Leu Arg Met Leu Glu Glu Ser
 65                  70                  75

TCT TCA GAA GTG ACA TCG TCT TCG GCA CTG GGT TTG CCA CCG GCC ATG                469
Ser Ser Glu Val Thr Ser Ser Ser Ala Leu Gly Leu Pro Pro Ala Met
 80                  85                  90                  95

GTT ATG TCG CCG GAA TCC TTG GCG TCG CCC GAG TAT CGA GCC CTC GAG                517
Val Met Ser Pro Glu Ser Leu Ala Ser Pro Glu Tyr Arg Ala Leu Glu
                100                 105                 110

CTA TGG AGC TAC GAT GAC GGA ATC ACT TAT AAT ACA GCC CAG TCT CTG                565
Leu Trp Ser Tyr Asp Asp Gly Ile Thr Tyr Asn Thr Ala Gln Ser Leu
            115                 120                 125

CTG GGT GCA TGC AAT ATG CAA CAG CAA CAG CTA CAA CCT CAG CAA CCA                613
Leu Gly Ala Cys Asn Met Gln Gln Gln Gln Leu Gln Pro Gln Gln Pro
        130                 135                 140

CAT CCA GCA CCA CCG ACG CTC CCC ACG ATG CCT TTA CCA ATG CCT CCC                661
His Pro Ala Pro Pro Thr Leu Pro Thr Met Pro Leu Pro Met Pro Pro
    145                 150                 155

ACA ACA CCG AAA TCA GAA AAT GAA TCG ATG TCA TCA GGT CGA GAG GAA                709
Thr Thr Pro Lys Ser Glu Asn Glu Ser Met Ser Ser Gly Arg Glu Glu
160                 165                 170                 175

CTT TCG CCG GCT TCA AGC ATA AAT GGC TGC AGT GCT GAT GCT GAC GCC                757
Leu Ser Pro Ala Ser Ser Ile Asn Gly Cys Ser Ala Asp Ala Asp Ala
                180                 185                 190

AGA CGG CAG AAG AAA GGT CCT GCA CCT CGA CAG CAA GAG GAG CTA TGT                805
Arg Arg Gln Lys Lys Gly Pro Ala Pro Arg Gln Gln Glu Glu Leu Cys
            195                 200                 205

CTT GTC TGC GGC GAC AGA GCC TCC GGA TAC CAC TAC AAC GCA CTG ACG                853
Leu Val Cys Gly Asp Arg Ala Ser Gly Tyr His Tyr Asn Ala Leu Thr
        210                 215                 220

TGT GAA GGA TGC AAA GGA TTC TTC AGG CGG AGT GTC ACC AAA AAC GCA                901
Cys Glu Gly Cys Lys Gly Phe Phe Arg Arg Ser Val Thr Lys Asn Ala
    225                 230                 235

GTA TAT ATT TGT AAA TTT GGA CAT GCC TGT GAA ATG GAT ATG TAC ATG                949
Val Tyr Ile Cys Lys Phe Gly His Ala Cys Glu Met Asp Met Tyr Met
240                 245                 250                 255

AGG AGG AAA TGT CAA GAG TGT CGA TTA AAG AAA TGT CTA GCG GTA GGA                997
Arg Arg Lys Cys Gln Glu Cys Arg Leu Lys Lys Cys Leu Ala Val Gly
                260                 265                 270

ATG AGG CCT GAA TGT GTC ATA CAG GAG CCC AGT AAA AAT AAA GAC AGG               1045
Met Arg Pro Glu Cys Val Ile Gln Glu Pro Ser Lys Asn Lys Asp Arg
            275                 280                 285

CAA AGA CAA AAG AAA GAC AAA GGA ATA TTA TTA CCT GTT AGT ACG ACC               1093
Gln Arg Gln Lys Lys Asp Lys Gly Ile Leu Leu Pro Val Ser Thr Thr
        290                 295                 300

ACA GTC GAA GAC CAC ATG CCC CCG ATC ATG CAA TGT GAT CCA CCT CCG               1141
Thr Val Glu Asp His Met Pro Pro Ile Met Gln Cys Asp Pro Pro Pro
    305                 310                 315

CCC GAG GCC GCC AGG ATT CAC GAA GTC GTC CCG AGG TAT CTT TCG GAG               1189
Pro Glu Ala Ala Arg Ile His Glu Val Val Pro Arg Tyr Leu Ser Glu
320                 325                 330                 335

AAG CTG ATG GAG CAG AAC AGG CAG AAG AAC ATA CCA CCA TTG TCG GCG               1237
```

```
                                                                          -continued Lys Leu Met Glu Gln Asn Arg Gln Lys Asn Ile Pro Pro Leu Ser Ala
            340                 345             350

AAT CAG AAG TCT CTG ATC GCG AGG CTC GTG TGG TAC CAG GAG GGA TAT    1285
Asn Gln Lys Ser Leu Ile Ala Arg Leu Val Trp Tyr Gln Glu Gly Tyr
                355                 360             365

GAG CAG CCC TCC GAC GAG GAT CTC AAA AGA GTA ACG CAG ACT TGG CAG    1333
Glu Gln Pro Ser Asp Glu Asp Leu Lys Arg Val Thr Gln Thr Trp Gln
            370                 375             380

TCG GAT GAA GAG GAC GAG GAA TCC GAT CTA CCC TTC CGC CAG ATC ACG    1381
Ser Asp Glu Glu Asp Glu Glu Ser Asp Leu Pro Phe Arg Gln Ile Thr
        385                 390             395

GAG ATG ACG ATC TTA ACG GTC CAG TTG ATC GTC GAG TTC GCC AAG GGT    1429
Glu Met Thr Ile Leu Thr Val Gln Leu Ile Val Glu Phe Ala Lys Gly
400                 405             410                 415

CTA CCG GGC TTT TCG AAG ATA TCA CAG TCT GAT CAA ATC ACC TTA TTA    1477
Leu Pro Gly Phe Ser Lys Ile Ser Gln Ser Asp Gln Ile Thr Leu Leu
                420                 425             430

AAA GCC TCG TCC AGC GAG GTG ATG ATG CTG CGG GTG GCG AGG CGA TAC    1525
Lys Ala Ser Ser Ser Glu Val Met Met Leu Arg Val Ala Arg Arg Tyr
            435                 440             445

GAC GCC GCG TCC GAC AGC GTG CTG TTC GCC AAC AAC AAG GCG TAC ACG    1573
Asp Ala Ala Ser Asp Ser Val Leu Phe Ala Asn Asn Lys Ala Tyr Thr
        450                 455             460

CGC GAC AAC TAC CGC CAA GGC GGC ATG GCC TAC GTC ATC GAA GAC CTC    1621
Arg Asp Asn Tyr Arg Gln Gly Gly Met Ala Tyr Val Ile Glu Asp Leu
    465                 470             475

CTA CAC TTC TGC CGG TGC ATG TTC GCG ATG GGC ATG GAC AAT GTG CAC    1669
Leu His Phe Cys Arg Cys Met Phe Ala Met Gly Met Asp Asn Val His
480                 485             490                 495

TTT GCA CTG CTC ACG GCC ATC GTT ATA TTC TCA GAT CGG CCC GGG CTC    1717
Phe Ala Leu Leu Thr Ala Ile Val Ile Phe Ser Asp Arg Pro Gly Leu
                500                 505             510

GAG CAG CCG TCG CTG GTA GAA GAG ATC CAG AGA TAC TAC CTG AAC ACG    1765
Glu Gln Pro Ser Leu Val Glu Glu Ile Gln Arg Tyr Tyr Leu Asn Thr
            515                 520             525

TTG CGA ATT TAC ATC ATC AAC CAG AAC AGC GCG TCG TCG CGC TGC GCC    1813
Leu Arg Ile Tyr Ile Ile Asn Gln Asn Ser Ala Ser Ser Arg Cys Ala
        530                 535             540

GTG ATC TAC GGC AGG ATC CTG AGC GTG CTG ACC GAG CTA CGC ACG CTC    1861
Val Ile Tyr Gly Arg Ile Leu Ser Val Leu Thr Glu Leu Arg Thr Leu
    545                 550             555

GGC ACG CAA AAC TCC AAC ATG TGC ATC TCG CTG AAG CTG AAG AAC AGG    1909
Gly Thr Gln Asn Ser Asn Met Cys Ile Ser Leu Lys Leu Lys Asn Arg
560                 565             570                 575

AAG CTG CCG CCG TTC CTC GAG GAG ATC TGG GAC GTG GCG GAG GTG GCC    1957
Lys Leu Pro Pro Phe Leu Glu Glu Ile Trp Asp Val Ala Glu Val Ala
                580                 585             590

ACG ACG CAT CCC ACG GTG CTG CCG CCC ACC AAC CCG GTG GTG CTA TAGCC  2007
Thr Thr His Pro Thr Val Leu Pro Pro Thr Asn Pro Val Val Leu
            595                 600             605

TCCGCCCGCC CCAGGAGAGA ACGCTCATAG ACTGGCTAGT TTTAGTGAAC GTGCGCTGAT  2067

CCGTATTCGG TGACAGATTA GTGATTATAT GTGTTGTTGA ACGTTTGGAG AGTATATATA  2127

TAGTGTTGAC GGCGAGGCCC GTCCGGCCCC GTACTTGTTT CGTTTCTGAC CGGATGCTGC  2187

GTCGGTCGCG CCCTTGCGAC CACGATAAGA CTACTTTCTA TAAGTACGTC TCTAAATTGA  2247

GGCCCCAAGA ACCGGAAGCC TAACTAAGAT ACGACGGTTT ATTTTATCAC AGAGGAAACT  2307

GAAGTAATTA ATATATTAAC AGTTAACACA GGTTCAAAGC AGTTAGGCCG CTCCGGACTT  2367
```

-continued

```
CTCATGGTCT CAATAAGGCG GACGTATAAG AGTTACATAG AGAATAAAAT AATAATATAT   2427

GAAGAGATGT TTCTATTGGA TGGAATGCGT GATGTAAAGT TGATAGTTAT TTTTATTTAC   2487

CAAATTAATG AAGCGTCGGG TGTAGACCTT TTGTATGTGA TGTGGCGAGG AGTGGATCGC   2547

AGTGTCGGCC GCGTGCTCTC ACCAAAAGCG TGCGGTCGAC GCTAATAGTG CGATGGTTTT   2607

GGAATATGTT TGTTTATATA TAGTTTATGT GTGAGGTGTT ATCGTGTCCC GTCAATTTTA   2667

ATTTCGATTC GCGTTCATTC GTCCTGTGCT CGCTACTCAG ATTT                    2711
```

(2) INFORMATION FOR SEQ ID NO:3:

(i) SEQUENCE CHARACTERISTICS:
        (A) LENGTH: 606 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:3:

```
Met Arg Val Glu Asn Val Asp Asn Val Ser Phe Ala Leu Asn Gly Arg
 1               5                  10                  15

Ala Asp Glu Trp Cys Met Ser Val Glu Thr Arg Leu Asp Ser Leu Val
            20                  25                  30

Arg Glu Lys Ser Glu Val Lys Ala Tyr Val Gly Gly Cys Pro Ser Val
        35                  40                  45

Ile Thr Asp Ala Gly Ala Tyr Asp Ala Leu Phe Asp Met Arg Arg Arg
    50                  55                  60

Trp Ser Asn Asn Gly Gly Phe Pro Leu Arg Met Leu Glu Glu Ser Ser
65                  70                  75                  80

Ser Glu Val Thr Ser Ser Ser Ala Leu Gly Leu Pro Pro Ala Met Val
                85                  90                  95

Met Ser Pro Glu Ser Leu Ala Ser Pro Glu Tyr Arg Ala Leu Glu Leu
            100                 105                 110

Trp Ser Tyr Asp Asp Gly Ile Thr Tyr Asn Thr Ala Gln Ser Leu Leu
        115                 120                 125

Gly Ala Cys Asn Met Gln Gln Gln Leu Gln Pro Gln Gln Pro His
    130                 135                 140

Pro Ala Pro Pro Thr Leu Pro Thr Met Pro Leu Pro Met Pro Pro Thr
145                 150                 155                 160

Thr Pro Lys Ser Glu Asn Glu Ser Met Ser Ser Gly Arg Glu Glu Leu
                165                 170                 175

Ser Pro Ala Ser Ser Ile Asn Gly Cys Ser Ala Asp Ala Asp Ala Arg
            180                 185                 190

Arg Gln Lys Lys Gly Pro Ala Pro Arg Gln Gln Glu Glu Leu Cys Leu
        195                 200                 205

Val Cys Gly Asp Arg Ala Ser Gly Tyr His Tyr Asn Ala Leu Thr Cys
    210                 215                 220

Glu Gly Cys Lys Gly Phe Phe Arg Arg Ser Val Thr Lys Asn Ala Val
225                 230                 235                 240

Tyr Ile Cys Lys Phe Gly His Ala Cys Glu Met Asp Met Tyr Met Arg
                245                 250                 255

Arg Lys Cys Gln Glu Cys Arg Leu Lys Lys Cys Leu Ala Val Gly Met
            260                 265                 270

Arg Pro Glu Cys Val Ile Gln Glu Pro Ser Lys Asn Lys Asp Arg Gln
```

```
              275                 280                 285
Arg Gln Lys Lys Asp Lys Gly Ile Leu Leu Pro Val Ser Thr Thr Thr
    290                 295                 300

Val Glu Asp His Met Pro Pro Ile Met Gln Cys Asp Pro Pro Pro Pro
305                 310                 315                 320

Glu Ala Ala Arg Ile His Glu Val Val Pro Arg Tyr Leu Ser Glu Lys
                325                 330                 335

Leu Met Glu Gln Asn Arg Gln Lys Asn Ile Pro Pro Leu Ser Ala Asn
                340                 345                 350

Gln Lys Ser Leu Ile Ala Arg Leu Val Trp Tyr Gln Glu Gly Tyr Glu
                355                 360                 365

Gln Pro Ser Asp Glu Asp Leu Lys Arg Val Thr Gln Thr Trp Gln Ser
    370                 375                 380

Asp Glu Glu Asp Glu Glu Ser Asp Leu Pro Phe Arg Gln Ile Thr Glu
385                 390                 395                 400

Met Thr Ile Leu Thr Val Gln Leu Ile Val Glu Phe Ala Lys Gly Leu
                405                 410                 415

Pro Gly Phe Ser Lys Ile Ser Gln Ser Asp Gln Ile Thr Leu Leu Lys
                420                 425                 430

Ala Ser Ser Ser Glu Val Met Met Leu Arg Val Ala Arg Arg Tyr Asp
    435                 440                 445

Ala Ala Ser Asp Ser Val Leu Phe Ala Asn Asn Lys Ala Tyr Thr Arg
    450                 455                 460

Asp Asn Tyr Arg Gln Gly Gly Met Ala Tyr Val Ile Glu Asp Leu Leu
465                 470                 475                 480

His Phe Cys Arg Cys Met Phe Ala Met Gly Met Asp Asn Val His Phe
                485                 490                 495

Ala Leu Leu Thr Ala Ile Val Ile Phe Ser Asp Arg Pro Gly Leu Glu
                500                 505                 510

Gln Pro Ser Leu Val Glu Glu Ile Gln Arg Tyr Tyr Leu Asn Thr Leu
                515                 520                 525

Arg Ile Tyr Ile Ile Asn Gln Asn Ser Ala Ser Ser Arg Cys Ala Val
    530                 535                 540

Ile Tyr Gly Arg Ile Leu Ser Val Leu Thr Glu Leu Arg Thr Leu Gly
545                 550                 555                 560

Thr Gln Asn Ser Asn Met Cys Ile Ser Leu Lys Leu Lys Asn Arg Lys
                565                 570                 575

Leu Pro Pro Phe Leu Glu Glu Ile Trp Asp Val Ala Glu Val Ala Thr
                580                 585                 590

Thr His Pro Thr Val Leu Pro Pro Thr Asn Pro Val Val Leu
    595                 600                 605

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:4:

CGGAGGACTG TCCTCCG                                                 17
```